US007507529B2

(12) United States Patent
Kim et al.

(10) Patent No.: US 7,507,529 B2

(45) Date of Patent: Mar. 24, 2009

(54) OLIGONUCLEOTIDES ORIGINATING FROM SEQUENCES CODING FOR THE SURFACE COMPONENT OF PTLV ENVELOPE PROTEINS AND THEIR USES

(75) Inventors: Felix Jinhyun Kim, New York City, NY (US); Nicolas Gabriel Albert Manel, Montpellier (FR); Marc Khamous Michel Sitbon, Montpellier (FR)

(73) Assignees: Centre National de la Recherche Scientifique, Paris Cedex (FR); Universite de Montpellier II, Montpellier Cedex (FR)

( * ) Notice: Subject to any disclaimer, the term of this patent is extended or adjusted under 35 U.S.C. 154(b) by 132 days.

(21) Appl. No.: 10/512,340

(22) PCT Filed: Apr. 22, 2003

(86) PCT No.: PCT/FR03/01274

§ 371 (c)(1),
(2), (4) Date: Jun. 15, 2005

(87) PCT Pub. No.: WO03/088979

PCT Pub. Date: Oct. 30, 2003

(65) Prior Publication Data

US 2005/0287521 A1 Dec. 29, 2005

(30) Foreign Application Priority Data

Apr. 22, 2002 (FR) .................................. 02 05001

(51) Int. Cl.
*C12Q 1/68* (2006.01)
*C12P 19/34* (2006.01)

(52) U.S. Cl. ......................................... 435/6; 435/91.2

(58) Field of Classification Search ....................... None
See application file for complete search history.

(56) References Cited

FOREIGN PATENT DOCUMENTS

| | | |
|---|---|---|
| EP | 0 384 566 | 8/1990 |
| WO | 00/46403 | 8/2000 |

OTHER PUBLICATIONS

Perzova et al (British Journal of Haematology (Apr. 2000) 109(1)64-70).*

Ting et al (J. Virol. (1998) 72(12):9453-9458).*

E. Ramirez et al. "Genetic characterization and phylogeny of human T-cell lymphotropic virus type I from Chile" Virus Research, vol. 84, Mar. 20, 2002, XP001148390, p. 137, col. 1, 1.35 oligonucleotide SG294.

S. Dube et al., "Degerate and specific PCR assays for the detection of bovine leukaemia virus and primate T cell leukaemia/lymphoma virus pol DNA and RNA: phylogenetic comparisons of amplified sequences from cattle and primates from around the world" Journal of General Virology, vol. 78, 1997, pp. 1389-1398, XP002233752, abstract.

G. S. Gray et al., "Envelope gene sequence of HTLV-1 isolate MT-2 and its comparison with other HTLV-1 isolates." Virology, vol. 177, 1990, pp. 391-395, XP008014557, figure.

David L. Suarez, "Identification of hypervariable and conserved regions in the surface envelope gene in the bovine lentivirus", Virology, vol. 212, No. 2, 1995, pp. 728-733, XP002253831, ISSN: 0042-06822, in particular Table 2.

* cited by examiner

*Primary Examiner*—Kenneth R. Horlick
*Assistant Examiner*—David C Thomas
(74) *Attorney, Agent, or Firm*—Young & Thompson

(57) ABSTRACT

The invention relates to the use of oligonucleotides from the nucleotide sequences coding for the amino-terminal region of the surface component (SU) of envelope proteins of PTLV viruses in order to perform methods of detecting every PTLV strain or PTLV-related viruses, e.g. for the detection of novel PTLV variants or viruses comprising sequences related to PTLV SUs. The invention also relates to primer pairs which are used to perform said detection methods and the novel PTLV variants thus detected.

15 Claims, No Drawings

OLIGONUCLEOTIDES ORIGINATING FROM SEQUENCES CODING FOR THE SURFACE COMPONENT OF PTLV ENVELOPE PROTEINS AND THEIR USES

A subject of the present invention is the oligonucleotides originating from the nucleotide sequences coding for the amino-terminal region of the surface component of envelope proteins of the viruses of T lymphomas/leukaemias in primates, grouped together under the designation PTLV, and their uses within the context of the detection of any strain of PTLV or related viral strains.

The present invention results from the identification by the Inventors of peptide units of the SU which are suitable for the synthesis of oligonucleotides which can be used for the detection and amplification of pan-PTLV sequences comprising these units. The inventors have developed a method allowing the amplification of such sequences, their cloning and sequencing. The present invention allows, in particular, the detection of individual sequences present in a mixture of sequences of different types. Optimization for certain peptide units thus identified has already allowed the characterization of PTLV variants which had not yet been described, as well as detecting PTLV sequences the presence of which in the samples tested was not suspected. The generalized application of the present invention will allow the detection and characterization either of novel sequences belonging to the SU of PTLV, or of sequences which are already known in new pathological or non pathological contexts.

Research into sequences of human or primate retroviruses is of paramount importance in numerous contexts. In a non-exhaustive manner, this research concerns the screening of biological materials (products derived from blood, for example), diagnosis (research into the etiology of multiple syndromes covering leukaemias, degenerative diseases, autoimmune diseases, etc), epidemiological and anthropological studies of different human groups, the sequencing of genomes (composition and polymorphic retroviral markers of genomes), the screening of novel medicaments (definition of new targets), etc.

In the case of PTLVs, we will demonstrate two examples of the problems associated with the detection of their sequences. In the first example, individuals, generally grouped under the term "seroindeterminate", present an anti-HTLV immune response called "incomplete", directed against certain antigens only of PTLVs, while no sequence corresponding to PTLVs can be amplified from blood samples of these patients. In the best documented cases research into such sequences is carried out on the conserved regions of the gag, pol, env and tax genes. In the case of the envelope gene, the amino-terminal part of the SU is excluded from this approach because of its variability. The amino-terminal region, of the surface component (SU) of the envelopes of the retroviruses of human and non-human primates of HTLV and STLV type (grouped together here under the term PTLV) is in particular responsible for the recognition of the cell receptor or receptors of the envelope (Kim et al, 2000). To this day, no method of amplification in this region which is directly applicable to the three types of PTLV (application called pan-PTLV) has been described. Thus, in general only the amplification of units present in the most conserved parts of the transmembrane component of the envelope (TM) is considered. However, insofar as the variability of the SU is an essential element of the adaptive biology of the retrovirus, developing an approach based on its detection represents a particularly useful objective.

A subject of the present invention is the use of pairs of degenerate oligonucleotides in 5' and 3' orientation originating from the nucleotide sequences coding for the amino-terminal region of the surface component (SU) of the envelope proteins of the viruses of T lymphomas/leukaemias in primates, grouped together under the designation PTLV, these viruses also being designated HTLV in man and STLV in the monkey, namely the region corresponding to the protein fragments delimited on the N-terminal side by an amino acid situated between positions 75 to 90, and on the C-terminal side by an amino acid situated between positions 230 to 245 of the envelope proteins of the different strains of PTLVs, or of a virus carrying the sequences belonging to the SU of PTLVs, for the implementation of processes for detecting any strain of PTLV, namely any strain belonging to HTLV-1, HTLV-2, STLV-1, STLV-2, and STLV-3, as well as any strain of virus belonging to PTLVs, namely any strain the amino acid sequence of which is deduced from the nucleotide sequence coding for the amino-terminal region of the SU has an homology level of at least approximately 30% with the amino acid sequences coded by the corresponding nucleotide sequences in PTLVs, in particular for detecting novel variants of PTLVs, or a virus, novel or not novel, comprising sequences belonging to the SU of PTLVs, if appropriate in new pathological contexts, said processes comprising an amplification stage, starting from a biological sample capable of containing PTLVs, and with the abovementioned degenerate 5' and 3' oligonucleotides used as primers, of the number of copies of nucleotide fragments delimited in position 5' by the degenerate oligonucleotide in 5' orientation, and in position 3' by the degenerate oligonucleotide in 3' orientation, and an identification stage of the strain of PTLV contained in the biological sample from the abovementioned amplified nucleotide fragments.

A more particular subject of the invention is the abovementioned use of pairs of degenerate oligonucleotides as defined above, characterized in that said oligonucleotides are chosen from those comprising approximately 15 to approximately 30 nucleotides originating from the nucleotide sequences coding for protein fragments delimited on the N-terminal side by an amino acid situated between positions 75 to 90, and on the C-terminal side by an amino acid situated between positions 230 to 245 of the envelope proteins of the different strains of PTLVs, such as the envelope protein of the MT-2 strain of HTLV-1 represented by SEQ ID NO: 43, or the NRA strain of HTLV-2 represented by SEQ ID NO: 45, or the strain of STLV-3 represented by SEQ ID NO: 47, said degenerate oligonucleotides comprising a mixture of oligonucleotides originating from sequences coding for a determined region of approximately 5 to 10 amino acids of the envelope proteins of the different strains of PTLV, and which differ from each other by the substitution of at least one nucleotide by another in a manner such that each oligonucleotide is capable of coding for the abovementioned determined region originating from the protein fragments of the envelope proteins of the different strains of PTLVs, such as the envelope protein of the MT-2 strain of HTLV-1, or the NRA strain of HTLV-2, or the strain of STLV-3 which are mentioned above.

A more particular subject of the invention is also the abovementioned use of pairs of degenerate oligonucleotides as defined above, comprising approximately 15 to approximately 30 nucleotides originating from nucleotide sequences coding for polypeptide fragments of approximately 5 to approximately 10 amino acids originating from protein fragments delimited by the amino acids situated at positions 80 to 245, and more particularly at positions 83 to 241, of the envelope protein of the MT-2 strain of HTLV-1 (Gray et al., 1990, Virology, 177: 391-395; Genbank access No. M37747) represented by SEQ ID NO: 43.

Also, the invention relates more particularly to the abovementioned use of pairs of degenerate oligonucleotides as defined above, originating from nucleotide sequences coding for polypeptide fragments 83-88, 140-145, 222-228, and 237-241, of the envelope protein of the MT-2 strain of HTLV-1, namely the following fragments:

83-YL/VFPHW-88

140-NFTQ/REV-145

222-NYS/TCI/MVC-228

237-WHVLY-241

Also, the invention relates more particularly to the abovementioned use of degenerate oligonucleotides in 5' orientation originating from the DNA (+) strand coding for:

the polypeptide fragment 83-88 of the envelope protein of the MT-2 strain of HTLV-1, said oligonucleotides being chosen from those of following formula (I):

```
TAYBTNTTYCCNCAYTGG     (I)     SEQ ID NO: 5
```

in which:

Y represents C or T,

B represents C, G or T,

N represents A, C, G or T, such as the 5' oligonucleotide primers chosen from the following:

```
PTLVE5'83a    TAYBTNTTYCCNCACTGG   SEQ ID NO: 6
PTLVE5'83b    TAYBTNTTYCCNCATTGG   SEQ ID NO: 7
```

Y, B and N being as defined above, or the polypeptide fragment 140-145 of the envelope protein of the MT-2 strain of HTLV-1, said oligonucleotides being chosen from those of following formula (II):

```
AAYTTYACNCARGARGT     (II)     SEQ ID NO: 8
```

in which:

Y represents C or T,

R represents A or G,

N represents A, C, G or T, such as the 5' oligonucleotide primers chosen from the following:

```
PTLVE5'140a   AAYTTYACNCAAGAAGT   SEQ ID NO: 9
PTLVE5'140b   AAYTTYACNCAGGAAGT   SEQ ID NO: 10
PTLVE5'140c   AAYTTYACNCAAGAGGT   SEQ ID NO: 11
PTLVE5'140d   AAYTTYACNCAGGAGGT   SEQ ID NO: 12
```

Y and N being as defined above.

Also, the invention relates more particularly to the abovementioned use, of degenerate oligonucleotides in 3' orientation originating from the DNA (−) strand coding for:

the polypeptide fragment 140-145 of the envelope protein of the MT-2 strain of HTLV-1, said oligonucleotides being chosen from those of following formula (III):

```
NACYTCYTGNGTRAARTT       (III)   SEQ ID NO: 13
```

in which:

Y represents C or T,

R represents A or G,

N represents A, C, G or T, such as the 3' oligonucleotide primers chosen from the following:

```
PTLVE3'145a   NACYTCYTGNGTAAAATT   SEQ ID NO: 14
PTLVE3'145b   NACYTCYTGNGTGAAATT   SEQ ID NO: 15
PTLVE3'145c   NACYTCYTGNGTAAAGTT   SEQ ID NO: 16
PTLVE3'145d   NACYTCYTGNGTGAAGTT   SEQ ID NO: 17
```

Y and N being as defined above, or the polypeptide fragment 222-228 of the envelope protein of the MT-2 strain of HTLV-1, said oligonucleotides being chosen from those of following formula (IV):

```
RMNACNATRCANSWRTARTT        (IV)   SEQ ID NO: 18
```

in which:

R represents A or G,

M represents A or C,

S represents C or G,

W represents A or T,

N represents A, C, G or T, such as the 3' oligonucleotide primers chosen from the following:

```
PTLVE3'228a   RMNACNATRCANSAATAATT   SEQ ID NO: 19
PTLVE3'228b   RMNACNATRCANSAGTAATT   SEQ ID NO: 20
PTLVE3'228c   RMNACNATRCANSAATAGTT   SEQ ID NO: 21
PTLVE3'228d   RMNACNATRCANSAGTAGTT   SEQ ID NO: 22
PTLVE3'228e   RMNACNATRCANSTATAATT   SEQ ID NO: 23
PTLVE3'228f   RMNACNATRCANSTGTAATT   SEQ ID NO: 24
PTLVE3'228g   RMNACNATRCANSTATAGTT   SEQ ID NO: 25
PTLVE3'228h   RMNACNATRCANSTGTAGTT   SEQ ID NO: 26
```

R, M, S, and N being as defined above, or the polypeptide fragment 237-241 of the envelope protein of the MT-2 strain of HTLV-1, said oligonucleotides being chosen from those of following formula (V):

```
RTANARNACRTGCCA       (V)      SEQ ID NO: 27
```

in which:

R represents A or G,

N represents A, C, G or T, such as the 3' oligonucleotide primers chosen from the following:

```
PTLVE3'241a       RTANARNACATGCCA
PTLVE3'241b       RTANARNACGTGCCA
```

R, and N being as defined above.

The invention also relates to the abovementioned use of oligonucleotides as defined above, comprising at their 5' end a sequence comprising a restriction site, such as the EcoRI site, of sequence GAATTC, or the BamHI site, of sequence GGATCC.

Therefore, the invention relates more particularly to the abovementioned use of oligonucleotides as defined above, characterized in that the 5' oligonucleotides originating from the DNA (+) strand corresponding to the polypeptide fragments 83-88 or 140-145 comprise at 5' a sequence GGAAGAATTC, and in that the 3' oligonucleotides originating from the DNA (−) strand corresponding to the polypeptide fragments 140-145, 222-228, and 237-241 comprise at 5' a sequence GGAAGGATCC.

A subject of the invention is also the abovementioned use of oligonucleotides as defined above as probes, if appropriate labeled, for the implementation of processes for detecting the abovementioned PTLV and related strains.

The invention also relates to the abovementioned use of oligonucleotides as defined above, as pairs of nucleotide, primers for the implementation of polymerase chain reactions (PCR) for the detection of any strain of PTLV, as well as any strain of virus comprising the sequences belonging to the SU of PTLVs.

A more particular subject of the invention is the abovementioned use of pairs of primers chosen in such a way that:

the degenerate 5' oligonucleotides correspond to a mixture of 5' oligonucleotides originating from a same determined nucleotide region comprising approximately 15 to approximately 30 nucleotides originating from the DNA (+) strand and coding for the polypeptide fragments of approximately 5 to approximately 10 amino acids originating from protein fragments delimited on the N-terminal side by an amino acid situated between positions 75 to 90, and on the C-terminal side by an amino acid situated between positions 135 to 150 of the envelope proteins of the different strains of PTLVs, in particular coding for the polypeptide fragments of approximately 5 to approximately 10 amino acids originating from the protein fragment delimited on the N-terminal side by the amino acid situated at position 83 and on the C-terminal side by the amino acid situated at position 145 of the envelope protein of the MT-2 strain of HTLV-1, said 5' oligonucleotides being such that they differ from each other by the substitution of at least one nucleotide by another such that each oligonucleotide is capable of coding for the abovementioned determined region originating from protein fragments of the envelope proteins of different strains of PTLVs, such as the envelope protein of the MT-2 strain of HTLV-1, or the NRA strain of HTLV-2, or the strain of STLV-3 which are mentioned above, the degenerate 3' oligonucleotides correspond to a mixture of 3' oligonucleotides originating from a same determined nucleotide region comprising approximately 15 to approximately 30 nucleotides originating from the DNA (−) strand and coding for the polypeptide fragments of approximately 5 to approximately 10 amino acids originating from protein fragments delimited on the N-terminal side by an amino acid situated between positions 125 to 145, and on the C-terminal side by an amino acid situated between positions 230 to 245 of the envelope proteins of the different strains of PTLVs, in particular coding for the polypeptide fragments of approximately 5 to approximately 10 amino acids originating from the protein fragment delimited on the N-terminal side by the amino acid situated at position 140 and on the C-terminal side by the amino acid situated at position 241 of the envelope protein of the MT-2 strain of HTLV-1, said 3' oligonucleotides being such that they differ from each other by the substitution of at least one nucleotide by another such that each oligonucleotide is capable of coding for the abovementioned determined region originating from the protein fragments of the envelope proteins of the different strains of PTLVs, such as the envelope protein of the MT-2 strain of HTLV-1, or the NRA strain of HTLV-2, or the strain of STLV-3 which are mentioned above, it being understood that said abovementioned 5' and 3' primers cannot be complementary to each other.

The invention relates more particularly to the abovementioned use of pairs of degenerate oligonucleotides as defined above, characterized in that the degenerate 5' oligonucleotides are chosen from the abovementioned 5' oligonucleotides of formulae (I) and (II), and in that the degenerate 3' oligonucleotides are chosen from the abovementioned 3' oligonucleotides of formulae (III) to (V).

The invention relates more particularly to the abovementioned use of pairs of primers as defined above, characterized in that the 5' primer is chosen from the 5' oligonucleotides originating from the DNA (+) strand corresponding to the polypeptide fragments 83-88 or 140-145 defined above, such that the primers PTLVE 5'83 a and b and PTLVE 5' 140 a to d mentioned above, and in that the 3' primer is chosen from the 3' oligonucleotides originating from the DNA (−) strand corresponding to the polypeptide fragments 140-145, 222-228 or 237-241 defined above, such as the primers PTLVE 3'145 a to d, PTLV3'228 a to h, and PTLVE 3'145 a to d, PTLV 3'228 a to h, and PTLVE 3'241 a and b mentioned above.

A more particular subject of the invention is the abovementioned use of pairs of degenerate oligonucleotides as defined above, said oligonucleotides being chosen in such a way that they allow the amplification, starting from a biological sample capable of containing the DNA of PTLV, of nucleotide sequences coding for the protein fragments comprising a sequence delimited on the N-terminal side by the amino acid situated in position 89, and on the C-terminal side by the amino acid situated in position 139 of the envelope protein of the MT-2 strain of HTLV-1 represented by SEQ ID NO: 43, or comprising an analogous sequence comprised in the envelope protein of a strain of PTLV other than HTLV-1, such as the sequence delimited on the N-terminal side by the amino acid situated in position 85, and on the C-terminal side by the amino acid situated in position 135 of the envelope protein of the NRA strain of HTLV-2 represented by SEQ ID NO: 45, or the sequence delimited on the N-terminal side by the amino acid situated in position 88, and on the C-terminal side by the amino acid situated in position 144 of the envelope protein of the strain of STLV-3 represented by SEQ ID NO: 47.

A more particular subject of the invention is also the abovementioned use of pairs of degenerate oligonucleotides as defined above, characterized in that the degenerate 5' oligonucleotides are chosen from the 5' oligonucleotides of formula (I) mentioned above, and in that the degenerate 3' oligonucleotides are chosen from the 3' oligonucleotides of formulae (III) to (V) mentioned above.

The invention relates more particularly to the abovementioned use of pairs of degenerate oligonucleotides as defined above, characterized in that:

the degenerate 5' oligonucleotides are those of following formula (I):

```
PTLVE5'83b    TAYBTNTTYCCNCATTGG  SEQ ID NO: 5
```

Y, B and N being as defined above, the degenerate 3' oligonucleotides are those of following formula (III):

```
PTLVE3'145a        NACYTCYTGNGTAAAATT
```

Y and N being as defined above.

The invention also relates to the oligonucleotides as defined above, as such.

Therefore, a more particular subject of the invention is the oligonucleotides as defined above, corresponding:

to the degenerate oligonucleotides in 5' orientation originating from the DNA(+) strand coding for:

the polypeptide fragment 83-88 of the envelope protein of the MT-2 strain of HTLV-1, said oligonucleotides being chosen from those of following formula (I):

```
TAYBTNTTYCCNCAYTGG     (I)     SEQ ID NO: 5
```

in which:

Y represents C or T,

B represents C, G or T,

N represents A, C, G or T, such as the 5' oligonucleotide primers chosen from the following:

```
PTLVE5'83a    TAYBTNTTYCCNCACTGG   SEQ ID NO: 6
PTLVE5'83b    TAYBTNTTYCCNCATTGG   SEQ ID NO: 7
```

Y, B and N being as defined above, the polypeptide fragment 140-145 of the envelope protein of the MT-2 strain of HTLV-1, said oligonucleotides being chosen from those of following formula (II):

```
AAYTTYACNCARGARGT     (II)     SEQ ID NO: 8
```

in which:

Y represents C or T,

R represents A or G,

N represents A, C, G or T, such as the 5' oligonucleotide primers chosen from the following:

```
PTLVE5'140a   AAYTTYACNCAAGAAGT   SEQ ID NO: 9
PTLVE5'140b   AAYTTYACNCAGGAAGT   SEQ ID NO: 10
PTLVE5'140c   AAYTTYACNCAAGAGGT   SEQ ID NO: 11
PTLVE5'140d   AAYTTYACNCAGGAGGT   SEQ ID NO: 12
```

Y and N being as defined above, to the degenerate oligonucleotides in 3' orientation originating from the DNA(−) strand coding for:

the polypeptide fragment 140-145 of the envelope protein of the MT-2 strain of HTLV-1, said oligonucleotides being chosen from those of following formula (III):

```
NACYTCYTGNGTRAARTT     (III)     SEQ ID NO: 13
```

in which:

Y represents C or T,

R represents A or G,

N represents A, C, G or T, such as the 3' oligonucleotide primers chosen from the followings:

```
PTLVE3'145a   NACYTCYTGNGTAAAATT   SEQ ID NO: 14
PTLVE3'145b   NACYTCYTGNGTGAAATT   SEQ ID NO: 15
PTLVE3'145c   NACYTCYTGNGTAAAGTT   SEQ ID NO: 16
PTLVE3'145d   NACYTCYTGNGTGAAGTT   SEQ ID NO: 17
```

Y and N being as defined above, the polypeptide fragment 222-228 of the envelope protein of the MT-2 strain of HTLV-1, said oligonucleotides being chosen from those of following formula (IV):

```
RMNACNATRCANSWRTARTT     (IV)     SEQ ID NO: 18
```

in which:

R represents A or G,

M represents A or C,

S represents C or G,

W represents A or T,

N represents A, C, G or T, such as the 3' oligonucleotide primers chosen from the following:

```
PTLVE3'228a   RMNACNATRCANSAATAATT   SEQ ID NO: 19
PTLVE3'228b   RMNACNATRCANSAGTAATT   SEQ ID NO: 20
PTLVE3'228c   RMNACNATRCANSAATAGTT   SEQ ID NO: 21
PTLVE3'228d   RMNACNATRCANSAGTAGTT   SEQ ID NO: 22
PTLVE3'228e   RMNACNATRCANSTATAATT   SEQ ID NO: 23
PTLVE3'228f   RMNACNATRCANSTGTAATT   SEQ ID NO: 24
PTLVE3'228g   RMNACNATRCANSTATAGTT   SEQ ID NO: 25
PTLVE3'228h   RMNACNATRCANSTGTAGTT   SEQ ID NO: 26
```

R, M, S, and N being as defined above, the polypeptide fragment 237-241 of the envelope protein of the MT-2 strain of HTLV-1, said oligonucleotides being chosen from those of following formula (V):

```
RTANARNACRTGCCA     (V)     SEQ ID NO: 27
```

in which:

R represents A or G,

N represents A, C, G or T.

such as the 3' oligonucleotide primers chosen from the following:

```
PTLVE3'241a   RTANARNACATGCCA   SEQ ID NO: 28
PTLVE3'241b   RTANARNACGTGCCA   SEQ ID NO: 29
```

R, and N being as defined above.

A subject of the invention is also a process for detecting any strain of PTLV, namely any strain belonging to HTLV-1, HTLV-2, STLV-1, STLV-2, and STLV-3, as well as any strain of virus comprising the sequences belonging to the SU of PTLVs, as defined above, characterized in that it comprises:

the bringing into contact of a pair of degenerate 5' and 3' oligonucleotides as defined above, with the genomic DNA or complementary DNA derived from RNA extracts of the content of a biological sample (such as blood cells, bone marrow, biopsies, in particular of the skin or other organs, or smears) capable of containing PTLVs as defined above, the amplification of DNA fragments coding for a fragment of the envelope proteins of the different strains of PTLVs as defined above, the detection of the DNA fragments amplified during the previous stage, this detection being able to be correlated to the detection and if appropriate to the identification of PTLV as defined above in said biological sample.

The invention also relates to a process for detecting any strain of PTLV as defined above, characterized in that the amplification stage comprises the implementation of two amplification reactions, the second reaction being carried out on a sample of products obtained within the context of the first reaction using the same 5' oligonucleotides as in the case of the first reaction, and 3' oligonucleotides which are different from those used in the first reaction, namely the so-called “nested” 3' primers hybridizing with a region situated more upstream of the sequence coding for the SU than the primers 3' used in the first reaction.

A subject of the invention is also a process for detecting any strain of PTLV as defined above, characterized in that it comprises:

a first gene amplification reaction carried out using pairs of degenerate oligonucleotides chosen from the pairs:

oligonucleotides of formula (I)/oligonucleotides of formula (IV), or oligonucleotides of formula (I)/oligonucleotides of formula (V), or oligonucleotides of formula (II)/oligonucleotides of formula (V), and a second amplification stage of the number of copies of DNA fragments obtained during the previous stage using pairs of degenerate oligonucleotides chosen respectively from the pairs:

oligonucleotides of formula (I)/oligonucleotides of formula (III), or oligonucleotides of formula (I)/oligonucleotides of formula (III or IV), or oligonucleotides of formula (I)/oligonucleotides of formula (IV), the detection of the DNA fragments amplified during the previous stage, this detection being able to be correlated to the detection and if appropriate to the identification of PTLV in the biological sample.

The invention also relates to a process for detecting any strain of PTLV as defined above, characterized in that it comprises:

a first gene amplification reaction carried out using pairs of degenerate oligonucleotides chosen in such a way that:

the degenerate 5' oligonucleotides are those of following formula (I):

```
PTLVE5'83b    TAYBTNTTYCCNCATTGG   SEQ ID NO: 5
```

Y, B and N being as defined above, the degenerate 3' oligonucleotides are those of following formula (V):

```
PTLVE3'241b   RTANARNACGTGCCA      SEQ ID NO: 29
```

R, and N being as defined above, a second gene amplification reaction carried out using pairs of degenerate oligonucleotides chosen in such a way that:

the degenerate 5' oligonucleotides are those of following formula (I):

```
PTLVE5'83b    TAYBTNTTYCCNCATTGG   SEQ ID NO: 5
```

Y, B and N being as defined above, the degenerate 3' oligonucleotides are those of following formula (III):

```
PTLVE3'145a   NACYTCYTGNGTAAAATT   SEQ ID NO: 14
```

Y and N being as defined above.

The invention relates more particularly to a detection process as defined above, characterized in that the amplification stage is carried out under the following conditions:

denaturation at 94° C. for 5 minutes, a first PCR reaction under so-called <<touch down>> conditions carried out in a medium containing Taq polymerase or other DNA polymerases which function at high temperature, this first PCR reaction comprising:

15 <<touch down>> cycles together varying by the extension temperature which reduces by 1° C. at each cycle comprising:

a denaturation stage at 94° C. for 15 seconds, a combined stage of annealing and extension at a temperature varying between 65° C. and 50° C. for 20 seconds, 30 standard cycles comprising:

a denaturation stage at 94° C. for 15 seconds, an annealing stage at 50° C. for 30 seconds, an extension stage at 72° C. for 30 seconds, a second PCR reaction carried out on a sample of products obtained in the context of the abovementioned first PCR reaction using the same 5' primer as in the case of the previous PCR reaction, and a 3' primer which is different to that used in the previous PCR reaction, namely a so-called “nested” 3' primer hybridizing with a region situated more upstream of the sequence coding for the SU than the 3' primer used in the previous stage.

A more particular subject of the invention is a detection process as defined above, characterized in that the detection stage, and if appropriate the identification stage, is carried out under the following conditions:

direct ligation of the fragments amplified during the amplification stage in a plasmid such as pCR4-TOPO (Invitrogen), transformation of bacteria with the abovementioned plasmid comprising a marker gene such as a gene resistant to an antibiotic, in particular to kanamycin, subculturing the bacterial colonies (in particular between 10 and 100), culture, extraction of the DNA, and sequencing (in particular using the universal primers T3 or T7 in the case of the use of the vector pCR4-TOPO).

The invention also relates to a kit for the implementation of a detection process as defined above, characterized in that it comprises a pair of abovementioned degenerate oligonucleotides, and, if appropriate, the reagents necessary for the implementation of the PCR amplification reaction and for the detection of the amplified fragments.

A subject of the invention is also the application of the detection process defined above for the diagnosis of pathologies linked to an infection by a PTLV, or by a virus comprising sequences belonging to the SU of PTLV, in man or animals, such as hemopathies, autoimmune diseases, inflammatory diseases, degenerative diseases.

Therefore, the invention relates to any method of in vitro diagnosis of the abovementioned pathologies by implementation of a detection process defined above, the detection of amplified DNA fragments being able to be correlated to the diagnosis of said pathologies.

If appropriate, the in vitro diagnosis methods of the invention comprising an additional stage of identifying PTLV or viruses belonging to PTLVs present in the biological sample, by sequencing the amplified DNA fragments.

A subject of the invention is also the application of the detection process defined above, with the screening and the identification of novel infectious agents in man or animals, and more particularly of novel strains (or variants) of a virus which can be classed in the PTLVs, or a virus comprising sequences belonging to the SU of PTLVs.

The abovementioned methods of screening and identification of novel infectious agents are carried out by the implementation of a detection process defined above and comprise an additional stage of identification of novel variants of PTLV or of a related virus by sequencing the amplified DNA fragments.

The invention also relates to the application of the detection process defined above by screening genes with a predisposition or a resistance to the pathologies in man or animals linked to the presence of sequences of PTLVs or of related sequences, or to an infection by a PTLV, such as hemopathies, autoimmune diseases, degenerative diseases.

A subject of the invention is also the application of the detection process defined above, to the screening or the design of novel therapeutic agents comprising entire or partial sequences of the envelope proteins of novel variants of PTLV thus detected.

The invention also relates to the application of the detection process as defined above, to the screening or the design of novel cell therapy vectors using the tropism proprieties of entire or partial sequences of the envelope proteins of novel variants of PTLV thus detected.

A subject of the invention is also the variants of type HTLV-1 as obtained by implementation of a detection process defined above, corresponding:

to the variant, the envelope protein of which is such that it comprises the following peptide sequence SEQ ID NO: 31:

```
I K K P N P N G G G Y Y L A S Y S D
P C S L K C P Y L G C Q S W T C P Y
T G A V S S P Y W K F Q Q D V
```

namely a sequence corresponding to the sequence delimited by the amino acids situated at positions 89 to 139 of the envelope protein of the MT-2 strain of HTLV-1, in which the arginine (R) residue in position 94, and the serine (S) residue in position 101, are replaced respectively by a proline (P) residue and a leucine (L) residue indicated in bold and underlined, and the nucleotide sequence of which coding for its envelope protein is such that it comprises the following sequence SEQ ID NO: 30:

```
ATT AAA AAG CCA AAC CCA AAT GGC GGA GGC TAT TAT TTA GCC TCT TAT TCA GAC
CCT TGT TCC TTA AAA TGC CCA TAC CTG GGG TGC CAA TCA TGG ACC TGC CCC TAT
ACA GGA GCC GTC TCC AGC CCC TAC TGG AAG TTT CAG CAA GAT GTC
```

namely a sequence corresponding to the sequence delimited by the nucleotides situated at positions 265 to 417 of the sequence coding for the envelope protein of the MT-2 strain of HTLV-1, in which G in position 281, C in position 302, and G in position 333, are replaced respectively by C, T, and A indicated in bold and underlined.

to the variant, the envelope protein of which is such that it comprises the following peptide sequence SEQ ID NO: 33:

```
V K K P N R N G G G Y Y L A S Y S D
P C S L K C P Y L G C Q S W T C P Y
T G A V S S P Y W K F Q Q D V
```

namely a sequence corresponding to the sequence delimited by the amino acids situated at positions 89 to 139 of the envelope protein of the MT-2 strain of HTLV-1, in which the isoleucine (I) residue in position 89, and the serine (S) residue in position 101, are replaced respectively by a valine (V) residue and a leucine (L) residue indicated in bold and underlined, and the nucleotide sequence of which coding for its envelope protein is such that it comprises the following sequence SEQ ID NO: 32:

```
GTT AAA AAG CCA AAC CGA AAT GGC GGA GGC TAT TAT TTA GCC TCT TAT TCA GAC
CCT TGT TCC TTA AAA TGC CCA TAC CTG GGG TGC CAA TCA TGG ACC TGC CCC TAT
ACA GGA GCC GTC TCC AGC CCC TAC TGG AAG TTT CAG CAA GAT GTC
```

namely a sequence corresponding to the sequence delimited by the nucleotides situated at positions 265 to 417 of the sequence coding for the envelope protein of the MT-2 strain of HTLV-1, in which A in position 266, C in position 302, and G in position 333, are replaced respectively by G, T, and A indicated in bold and underlined, to the variant, the envelope protein of which is such that it comprises the following peptide sequence SEQ ID NO: 35:

I K K P N R N G G G Y Y L A S Y S D

P C S L K C P Y L G C Q S W T C P Y

T G A V S S P Y W K F Q Q D V namely a sequence corresponding to the sequence delimited by the amino acids situated at positions 89 to 139 of the envelope protein of the MT-2 strain of HTLV-1, in which the serine (S) residue in position 101, is replaced by a leucine (L) residue indicated in bold and underlined, and the nucleotide sequence of which coding for its envelope protein is such that it comprises the following sequence SEQ ID NO: 34:

ATT AAA AAG CCA AAC CGA AAT GGC GGA GGC TAT TAT TTA GCC TCT TAT TCA GAC

CCT TGT TCC TTA AAA TGC CCA TAC CTG GGG TGC CAA TCA TGG ACC TGC CCC TAT

ACA GGA GCC GTC TCC AGC CCC TAC TGG AAG TTT CAA CAA GAT GTC namely a sequence corresponding to the sequence delimited by the nucleotides situated at positions 265 to 417 of the sequence coding for the envelope protein of the MT-2 strain of HTLV-1, in which C in position 302, G in position 333, and G in position 408, are replaced respectively by T, A, and A indicated in bold and underlined, to the variant, the envelope protein of which is such that it comprises the following peptide sequence SEQ ID NO: 37:

namely a sequence corresponding to the sequence delimited by the nucleotides situated at positions 265 to 417 of the sequence coding for the envelope protein of the MT-2 strain of HTLV-1, in which G in position 379, is replaced by C indicated in bold and underlined, to the variant, the envelope protein of which is such that it comprises the following peptide sequence SEQ ID NO: 39:

I K K P N R N G G G Y H S A S Y S D P

C S L K C P Y L G C Q S W T C P Y A G

A V S S P Y W K F Q Q D V N F T Q E V namely a sequence corresponding to the sequence delimited by the amino acids situated at positions 89 to 145 of the envelope protein of the MT-2 strain of HTLV-1, in which the tyrosine (Y) residue in position 100, and the threonine (T) residue in position 125, are replaced respectively by a histidine (H) residue and an alanine (A) residue indicated in bold and underlined, and the nucleotide sequence of which coding for its envelope protein is such that it comprises the following sequence SEQ ID NO: 38:

ATT AAA AAG CCA AAC CGA AAT GGC GGA GGC TAT CAT TCA GCC TCT TAT TCA

GAC CCT TGT TCC TTA AAG TGC CCA TAC CTG GGG TGC CAA TCA TGG ACC TGC

CCC TAT GCA GGA GCC GTC TCC AGC CCC TAC TGG AAG TTT CAG CAA GAT GTC

AAT TTT ACC CAG GAA GTA

I K K P N R N G G G Y Y L A S Y S D

P C S L K C P Y L G C Q S W T C P Y

T G P V S S P Y W K F Q Q D V namely a sequence corresponding to the sequence delimited by the amino acids situated at positions 89 to 139 of the envelope protein of the MT-2 strain of HTLV-1, in which the alanine (A) residue in position 127, is replaced by a proline (P) residue indicated in bold and underlined, and the nucleotide sequence of which coding for its envelope protein is such that it comprises the following sequence SEQ ID NO: 36:

namely a sequence corresponding to the sequence delimited by the nucleotides situated at positions 265 to 435 of the sequence coding for the envelope protein of the MT-2 strain of HTLV-1, in which T in position 298, A in position 373, T in position 426, A in position 429, and T in position 435, are replaced respectively by C, G, C, G, and A indicated in bold and underlined.

A subject of the invention is also the variant of type HTLV-2 as obtained by implementation of a detection process defined above, characterized in that:

its envelope protein is such that it comprises the following peptide sequence SEQ ID NO: 41:

GTT AAA AAG CCA AAC CGA AAT GGC GGA GGC TAT TAT TTA GCC TCT TAT TCA GAC

CCT TGT TCC TTA AAA TGC CCA TAC CTG GGG TGC CAA TCA TGG ACC TGC CCC TAT

ACA GGA CCC GTC TCC AGC CCC TAC TGG AAG TTT CAG CAA GAT GTC

I R K P N R Q G L G Y Y S P S Y N D

P C S L Q C P Y L G S Q S W T C P Y

T A P V S T P S W N F H S D V namely a sequence corresponding to the sequence delimited by the amino acids situated at positions 85 to 135 of the envelope protein of the prototype NRA strain of HTLV-2 (described by Lee et al., 1993. Virology 196, 57-69; Genbank access No. L20734.1), in which the following residues: lysine (K) in position 86, cysteine (C) in position 113, glycine (G) in position 122, serine (S) in position 126, and lysine (K) in position 130, are replaced respectively by the following residues: arginine (R), serine (S), alanine (A), threonine (T), and asparagine (N) indicated in bold and underlined, the nucleotide sequence coding for its envelope protein is such that it comprises the following sequence SEQ ID NO: 40:

ATA AGA AAG CCA AAC AGA CAG GGC CTA GGG TAC TAC TCG CCT TCC TAC AAT GAC

CCT TGC TCG CTA CAA TGC CCC TAC TTG GGC TCC CAA TCA TGG ACA TGC CCA TAC

ACG GCC CCC GTC TCC ACT CCA TCC TGG AAT TTT CAT TCA GAT GTA namely a sequence corresponding to the sequence delimited by the nucleotides situated at positions 253 to 405 of the sequence coding for the envelope protein of the NRA strain of HTLV-2, in which A in position 257, G in position 258, T in position 267, A in position 282, C in position 294, T in position 300, A in position 333, G in position 338, G in position 365, G in position 377, G in position 390, and C in position 396, are replaced respectively by G, A, C, G, T, C, G, C, C, C, T, and T indicated in bold and underlined.

The invention also relates to the polypeptides delimited on the N-terminal side by an amino acid situated between positions 75 to 90, and on the C-terminal side by an amino acid situated between positions 230 to 245 of the envelope proteins of the different strains of PTLVs, such as the envelope protein of the MT-2 strain of HTLV-1 represented by SEQ ID NO: 43, or the NRA strain of HTLV-2 represented by SEQ ID NO: 45, or the strain of STLV-3 represented by SEQ ID NO: 47, or a virus carrying the sequences belonging to the SUs of PTLVs, or delimited on the N-terminal side by an amino acid situated between positions 75 to 90, and on the C-terminal side by an amino acid situated between positions 135 to 150 of said envelope proteins of the different strains of PTLVs.

A subject of the invention is also the polypeptides defined above, chosen from:

the polypeptide delimited on the N-terminal side by the amino acid situated at position 83 or 89, and on the C-terminal side by the amino acid situated at position 139 or 145, of the envelope protein of the MT-2 strain of HTLV-1 represented by SEQ ID NO: 43, the polypeptide delimited on the N-terminal side by the amino acid situated at position 79 or 85, and on the C-terminal side by the amino acid situated at position 135 or 141, of the envelope protein of the NRA strain of HTLV-2 represented by SEQ ID NO: 45, the polypeptide delimited on the N-terminal side by the amino acid situated at position 82 or 88, and on the C-terminal side by the amino acid situated at position 138 or 144, of the envelope protein of the strain of STLV-3 represented by SEQ ID NO: 47.

The invention relates also to the polypeptides coded by the DNA fragments amplified within the context of the detection process defined above, of variants of type HTLV-1 to HTLV-2 mentioned above, characterized in that they comprise the following peptide sequences:

polypeptide 1 (SEQ ID NO: 31):

I K K P N P N G G G Y Y L A S Y S D

P C S L K C P Y L G C Q S W T C P Y

T G A V S S P Y W K F Q Q D V namely a sequence corresponding to the sequence delimited by the amino acids situated at positions 89 to 139 of the envelope protein of the MT-2 strain of HTLV-1, in which the arginine (R) residue in position 94, and the serine (S) residue in position 101, are replaced respectively by a proline (P) residue and a leucine (L) residue indicated in bold and underlined, polypeptide 2 (SEQ ID NO: 33):

V K K P N R N G G G Y Y L A S Y S D

P C S L K C P Y L G C Q S W T C P Y

T G A V S S P Y W K F Q Q D V namely a sequence corresponding to the sequence delimited by the amino acids situated at positions 89 to 139 of the envelope protein of the MT-2 strain of HTLV-1, in which the isoleucine (I) residue in position 89, and the serine (S) residue in position 101, are replaced respectively by a valine (V) residue and a leucine (L) residue indicated in bold and underlined, polypeptide 3 (SEQ ID NO: 35):

I K K P N R N G G G Y Y L A S Y S D

P C S L K C P Y L G C Q S W T C P Y

T G A V S S P Y W K F Q Q D V namely a sequence corresponding to the sequence delimited by the amino acids situated at positions 89 to 139 of the envelope protein of the MT-2 strain of HTLV-1, in which the serine (S) residue in position 101, is replaced by a leucine (L) residue indicated in bold and underlined, polypeptide 4 (SEQ ID NO: 37):

```
I K K P N R N G G G Y Y L A S Y S D
P C S L K C P Y L G C Q S W T C P Y
T G P V S S P Y W K F Q Q D V
```

namely a sequence corresponding to the sequence delimited by the amino acids situated at positions 89 to 139 of the envelope protein of the MT-2 strain of HTLV-1, in which the alanine (A) residue in position 127, is replaced by a proline (P) residue indicated in bold and underlined, polypeptide 5 (SEQ ID NO: 39):

```
I K K P N R N G G G Y H S A S Y S D P
C S L K C P Y L G C Q S W T C P Y A G
A V S S P Y W K F Q Q D V N F T Q E V
```

namely a sequence corresponding to the sequence delimited by the amino acids situated at positions 89 to 145 of the envelope protein of the MT-2 strain of HTLV-1, in which the tyrosine (Y) residue in position 100, and the threonine (T) residue in position 125, are replaced respectively by a histidine (H) residue and an alanine (A) residue indicated in bold and underlined, polypeptide 6 (SEQ ID NO: 41):

```
I R K P N R Q G L G Y Y S P S Y N D
P C S L Q C P Y L G S Q S W T C P Y
T A P V S T P S W N F H S D V
```

namely a sequence corresponding to the sequence delimited by the amino acids situated at positions 85 to 135 of the envelope protein of the prototype NRA strain of HTLV-2, in which the following residues: lysine (K) in position 86, cysteine (C) in position 113, glycine (G) in position 122, serine (S) in position 126, and lysine (K) in position 130, are replaced respectively by the following residues: arginine (R), serine (S), alanine (A), threonine (T), and asparagine (N) indicated in bold and underlined.

A subject of the invention is also the nucleic acids characterized in that they code for a polypeptide as defined above.

The invention relates more precisely to the abovementioned nucleic acids, comprising the following nucleotide sequences:

nucleic acid 1 a (SEQ ID NO: 30):

```
ATT AAA AAG CCA AAC CCA AAT GGC GGA GGC TAT TAT TTA GCC TCT TAT TCA GAC
CCT TGT TCC TTA AAA TGC CCA TAC CTG GGG TGC CAA TCA TGG ACC TGC CCC TAT
ACA GGA GCC GTC TCC AGC CCC TAC TGG AAG TTT CAG CAA GAT GTC
```

namely a sequence corresponding to the sequence delimited by the nucleotides situated at positions 265 to 417 of the sequence coding for the envelope protein of the MT-2 strain of HTLV-1, in which G in position 281, C in position 302, and G in position 333, are replaced respectively by C, T, and A indicated in bold and underlined, or any nucleotide sequence derived by degeneration of the genetic code and coding for the abovementioned polypeptide 1, nucleic acid 2 a (SEQ ID NO: 32):

```
GTT AAA AAG CCA AAC CGA AAT GGC GGA GGC TAT TAT TTA GCC TCT TAT TCA GAC
CCT TGT TCC TTA AAA TGC CCA TAC CTG GGG TGC CAA TCA TGG ACC TGC CCC TAT
ACA GGA GCC GTC TCC AGC CCC TAC TGG AAG TTT CAG CAA GAT GTC
```

namely a sequence corresponding to the sequence delimited by the nucleotides situated at positions 265 to 417 of the sequence coding for the envelope protein of the MT-2 strain of HTLV-1, in which A in position 266, C in position 302, and G in position 333, are replaced respectively by G, T, and A indicated in bold and underlined, or any nucleotide sequence derived by degeneration of the genetic code and coding for the abovementioned polypeptide 2, nucleic acid 3 a (SEQ ID NO: 34):

```
ATT AAA AAG CCA AAC CGA AAT GGC GGA GGC TAT TAT TTA GCC TCT TAT TCA GAC
CCT TGT TCC TTA AAA TGC CCA TAC CTG GGG TGC CAA TCA TGG ACC TGC CCC TAT
ACA GGA GCC GTC TCC AGC CCC TAC TGG AAG TTT CAA CAA GAT GTC
```

namely a sequence corresponding to the sequence delimited by the nucleotides situated at positions 265 to 417 of the sequence coding for the envelope protein of the MT-2 strain of HTLV-1, in which C in position 302, G in position 333, and G in position 408, are replaced respectively by T, A, and A indicated in bold and underlined, or any nucleotide sequence derived by degeneration of the genetic code and coding for the polypeptide 3 of claim 24, nucleic acid 4 a (SEQ ID NO: 36):

```
GTT AAA AAG CCA AAC CGA AAT GGC GGA GGC TAT TAT TTA GCC TCT TAT TCA GAC
CCT TGT TCC TTA AAA TGC CCA TAC CTG GGG TGC CAA TCA TGG ACC TGC CCC TAT
ACA GGA CCC GTC TCC AGC CCC TAC TGG AAG TTT CAG CAA GAT GTC
```

namely a sequence corresponding to the sequence delimited by the nucleotides situated at positions 265 to 417 of the sequence coding for the envelope protein of the MT-2 strain of HTLV-1, in which G in position 379, is replaced by C indicated in bold and underlined, or any nucleotide sequence derived by degeneration of the genetic code and coding for the abovementioned polypeptide 4, nucleic acid 5 a (SEQ ID NO: 38):

```
ATT AAA AAG CCA AAC CGA AAT GGC GGA GGC TAT CAT TCA GCC TCT TAT TCA
GAC CCT TGT TCC TTA AAG TGC CCA TAC CTG GGG TGC CAA TCA TGG ACC TGC
CCC TAT GCA GGA GCC GTC TCC AGC CCC TAC TGG AAG TTT CAG CAA GAT GTC
AAT TTT ACC CAG GAA GTA
```

namely a sequence corresponding to the sequence delimited by the nucleotides situated at positions 265 to 435 of the sequence coding for the envelope protein of the MT-2 strain of HTLV-1, in which T in position 298, A in position 373, T in position 426, A in position 429, and T in position 435, are replaced respectively by C, G, C, G, and A indicated in bold and underlined, or any nucleotide sequence derived by degeneration of the genetic code and coding for the abovementioned polypeptide 5, nucleic acid 6 a (SEQ ID NO: 40):

```
ATA AGA AAG CCA AAC AGA CAG GGC CTA GGG TAC TAC TCG CCT TCC TAC AAT GAC
CCT TGC TCG CTA CAA TGC CCC TAC TTG GGC TCC CAA TCA TGG ACA TGC CCA TAC
ACG GCC CCC GTC TCC ACT CCA TCC TGG AAT TTT CAT TCA GAT GTA
```

namely a sequence corresponding to the sequence delimited by the nucleotides situated at positions 253 to 405 of the sequence coding for the envelope protein of the NRA strain of HTLV-2, in which A in position 257, G in position 258, T in position 267, A in position 282, C in position 294, T in position 300, A in position 333, G in position 338, G in position 365, G in position 377, G in position 390, and C in position 396, are replaced respectively by G, A, C, G, T, C, G, C, C, C, T, and T indicated in bold and underlined, or any nucleotide sequence derived by degeneration of the genetic code and coding for the abovementioned polypeptide 6.

The invention also relates to the polyclonal or monoclonal antibodies directed against a novel variant of type HTLV-1 or HTLV 2 as defined above, or against a polypeptide defined above, said antibodies being as obtained by immunization of an appropriate animal with an abovementioned polypeptide.

A subject of the invention is also any pharmaceutical composition, in particular therapeutic vaccines or vectors, formed from of the novel variants of type HTLV-1 or HTLV-2 as defined above, and more particularly any pharmaceutical composition comprising a polypeptide according to the invention as defined above, in particular the polypeptides 1 to 6 defined above, or a nucleic acid 1a to 6a defined above, or the abovementioned antibodies, if appropriate in combination with a pharmaceutically acceptable vehicle.

The invention also relates to the use of the novel variants of type HTLV-1 or HTLV-2 as defined above, or the polypeptides according to the invention as defined above, in particular the polypeptides 1 to 6, or the nucleic acids 1a to 6a defined above, or the abovementioned antibodies, for the preparation of medicaments intended for the prevention or treatment of infections of an individual by the abovementioned PTLVs, as well as the pathologies defined above linked to infection by these PTLVs.

The invention is further illustrated by the detailed description which follows for obtaining primers according to the invention and of their use for the detection of novel variants of HTLV.

I—Development of Molecular Tools and Strategies for the Detection of PAN-PTLV Sequences by Amplification, Cloning and Sequencing of Nucleotide Sequences Related to the Su of PTLV Envelopes.

1. Screening for Peptide Units Conserved in the N-Terminus of the SU of PTLV

The main question resolved by the inventors is the development of tools and of a method allowing the amplification, cloning and identification of any nucleotide sequence related to the SU of PTLVs which is responsible for the recognition of their cell receptor (Kim et al., 2000). To this end, the inventors looked for peptide units conserved in the SU of PTLV envelopes in order to deduce therefrom nucleotide sequences which allow representation of them all. These peptide units should ideally meet the following 5 criteria, in decreasing order of importance:

To be conserved in most, if not all, of the PTLV envelope sequences already described. Such a conservation would be a guarantee of their potential effectiveness in the detection of new sequences of PTLV type.

To represent at least 5 conserved amino acids from the SU of PTLVs, in order to derive therefrom a minimum sequence of 15 nucleotides. Given the complexity of the eukaryotic genomes, this minimum of 15 nucleotides is required to allow the specific detection of a given nucleotide sequence.

To allow the amplification of sequences situated upstream of the C I/M V C unit which is conserved in the SU of PTLVs and seems to be analogous to the CWLC unit described in the SU of MuLVs (Sitbon et al., 1991). This unit seems in fact, to mark a hinge region between, upstream of it, the part of the SU responsible for the recognition of the receptor and, downstream of it, the carboxyl-terminal domains of the SU involved in the association with the TM and stages of viral entry subsequent to the recognition of the receptor (Battini, et al., 1992; Battini et al., 1995; Lavillette et al., 1998; Kim et al., 2000; Lavillette et al., 2001). To be sufficiently distant from each other to allow the amplification of a fragment whose length would increase the chances of detection of a possible polymorphism between different sequences.

To be situated so as to allow two successive DNA amplification reactions, the second of which, nested, is produced from products of the first amplification, and allows the amplification of a fragment internal to the first fragment amplified. This nested amplification allows an increase in the probability of amplification of a fragment which corresponds well to a sequence related to the SU of PTLVs.

According to these criteria, the inventors have identified the following amino acid units, present in all or almost all of the known SUs of PTLV, and being able to help in the development of this strategy:

Peptide unit 1: Y L/V F P H W
Peptide unit 2: N F T Q/R E V
Peptide unit 3: N Y S/T C I/M V C
Peptide unit 4: W H V L Y 2. Degenerated Synthesis Oligonucleotides Corresponding to the Units Conserved in the Amino-terminal Part of the SU of PTLVs Using amino acid sequences of the conserved peptide units identified above and following the nucleotide correspondence in the application of the eukaryotic genetic code, the inventors determined degenerated nucleotide sequences (DNS) which served as the basis for the design of synthesis oligonucleotides (SO). Several criteria governed the design of SO corresponding to these DNS:

When the multiplication of the degenerated positions in a DNS would make the complexity of the corresponding SO exceed 512 oligonucleotides in the synthesis mixture, the synthesis of supplementary SO for this DNS is then carried out to remove some of this complexity.

The synthesis of one or 2 supplementary OS, to a limit of 4 SO per DNS, is carried out even for complexities less than 512, when these supplementary SO significantly remove the complexity of the initial degenerated OS.

The sequences of the 5' SO, the extension of which by the DNA polymerases must correspond to the amino acids situated upstream of the peptide unit considered (units 1 and 2), are those of the DNA (+) strand, while those of the 3' SO, the extension of which must correspond to the amino acids situated upstream of the peptide unit considered (units 2, 3 and 4), are those of the DNA (−) strand. The SO corresponding to the peptide unit 2 were synthesized on the two strands, in order to be able to carry out an extension in both directions.

Each SO comprises supplementary nucleotides allowing the introduction at 5' of the sequence corresponding to a restriction site, EcoRI for the 5' OS, BamHI for the 3' SO, and in all the cases a GGAA 5'-terminal sequence favouring the binding of the polymerases and nucleases upstream of the restriction site.

According to these criteria, the SO PTLVE5' (83 a and b, 140 a to d) and PTLVE3' (145 a to d, 228 a to h, 241 a and b) (for Primate T-Leukemia Virus-like Env), defined above were synthesized respectively for elongations at 5' or 3' of the targeted unit.

3. Development of the Amplification Conditions with Oligonucleotides on Control Sequences For the development of the amplification of sequences recognized by the SO described above, the inventors used control plasmid DNA preparations containing the HTLV-1 sequence envelope and control preparations not having this sequence. The DNA amplification strategy chosen consists of linking two amplification reactions by a mixture of the Taq and Pwo polymerases on a thermal cycler under conditions called "touch-down" and combining 2 different SO pairs.

The first probative and reproducible amplification results (specific amplification of HTLV sequences without amplification on the control preparations) are those obtained with the combination of the SO PTLVE5'83b and PTLVE3'240b, for the first amplification reaction, followed by a $2^{nd}$ reaction combining the SO PTLVE5'83b and PTLVE3'146a on a sample of the $1^{st}$ reaction. In both cases the "touch-down" conditions include 15 cycles combining each denaturation at 94° C. followed by a stage of annealing and extension carried out at the same temperature, this temperature being comprised for each cycle between 65 and 50° C. with a decreasing step of 1° C. between the $1^{st}$ and the $15^{th}$ cycle. These 15 cycles are followed by 30 standard amplification cycles with an annealing temperature at 50° C. and an extension temperature at 72° C.

4. Construction and Sequencing of a Bank of Fragments Amplified from Amplification Reactions A sample of the $2^{nd}$ amplification reaction described above is used to generate a bank of the amplified sequences. To do this 4 μl of the 50 μl of the $2^{nd}$ reaction is used for ligation in a pCR4-TOPO type vector (Invitrogen) and transformation of bacteria. Between 10 and 100 colonies resistant to kanamycin are subcultured for each ligation and placed in culture. The plasmid DNA of each colony is analysed by sequencing using universal primer sequences T3 and T7 of the vector.

II—First Results Obtained from Human and Primate Samples

The conditions described above were applied to three types of DNA samples:

Samples of genomic DNA of "seroindeterminate patients", characterized by a serology suggesting a previous infection with HTLV but in whom no definitive diagnosis was able to be established. In these patients, in particular, research by DNA amplification of gag, pol or tax HT-LV sequences is negative.

Samples of genomic DNA of "HTLV-1 patients" in whom a characteristic HTLV-1 infection was identified.

Samples of genomic DNA of Agile Mangabey monkeys (Cercocebus Agilis) which have a positive PTLV serology and in which Tax HTLV-1 or STLV-L sequences were able to be amplified.

The application of the method described above allowed detection of the presence of SU type PTLV sequences in the three types of samples, including in the "seroindeterminate patients".

Analysis of the sequences and of their coding capacities at the level of the SU region concerned allowed the following observations to be made:

1. Results Obtained on "Seroindeterminate Patients"

By applying the method described above on the DNA of a "seroindeterminate patient" (sample No. 424), described as not having an HTLV type sequence, the inventors were however able to amplify and characterize SU type PTLV sequences.

At the nucleotide level, the sequences identified from sample No. 424 are of several types: HTLV-1 sequences identical to those already described in the literature and new variants. At the coding level, the nucleotide sequences translate into three types of sequences:

Amino acids sequences identical to those of the HTLV-1 strains already known.

Variants of HTLV-1 strains with 1 or 2 residues not described previously.

Variants of HTLV-1 strains with 1 or 2 residues described as common only to the HTLV-2 or STLV-L strains.

2. Results Obtained on "Typical HTLV-1 Patients"

At the nucleotide level, the amplified sequences from the sample originating from the "HTLV-1 patient" (sample No. 422) are either typically HTLV-1, as already described in the literature, or variants with repercussions for the coding capacity. At the coding level, the nucleotide sequences translate into three types of sequences:

Amino acids sequences identical to the known HTLV-1 strains.

HTLV-1 variants with 1 or 2 residues typical of HTLV-2, combined or not combined with residues never previously described.

HTLV-2 variants combining a few residues described as being common only to the HTLV-2 or STLV-L strains, this being combined or not combined with residues never previously described.

3. Results obtained on Cercocebus Agilis monkeys

The method of the invention also allowed amplification of the SU type PTLV sequences in all the Agile Mangabey monkeys (Cercocebus Agilis) tested which were identified as seropositive for PTLV. At the nucleotide level, the sequences amplified from these monkeys are either those of the isolates already described previously, or nucleotide variants with repercussions for the coding capacity. At the coding level, the nucleotide sequences translate into three types of sequences:

Amino acids sequences identical to the known HTLV-1 strains.

Amino acids sequences identical to the isolate STLV-3/CTO-604 recently described in a red-capped Mangabey (Cercocebus Torquatus) (Meertens et al., 2002)

Amino acid sequences of the STLV-3/CTO-604 type with 1 or 2 residues typical of HTLV-2

III—BIBLIOGRAPHY

1. Battini, J. L., O. Danos, and J. M. Heard. 1995. Receptor-binding domain of murine leukaemia virus envelope glycoproteins. J. Virol. 69(2):713-719.

2. Battini, J. L., J. M. Heard, and O. Danos. 1992. Receptor choice determinants in the envelope glycoproteins of amphotropic, xenotropic, and polytropic murine leukaemia viruses. J. Virol. 66(3):1468-75.

3. Kim, F. J., I. Seiliez, C. Denesvre, D. Lavillette, F. L. Cosset, and M. Sitbon. 2000. Definition of an amino-terminal domain of the human T-cell leukaemia virus type 1 envelope surface unit that extends the fusogenic range of an ecotropic murine leukaemia virus. J Biol. Chem. 275(31):23417-20.

4. Lavillette, D., M. Maurice, C. Roche, S. J. Russell, M. Sitbon, and F. L. Cosset. 1998. A proline-rich motif downstream of the receptor binding domain modulates conformation and fusogenicity of murine retroviral envelopes. J. Virol. 72(12):9955-65.

5. Lavillette, D., A. Ruggieri, S. J. Russell, and F. L. Cosset. 2000. Activation of a cell entry pathway common to type C mammalian retroviruses by soluble envelope fragments. J. Virol. 74(1):295-304.

6. Meertens, L., R. Mahieux, P. Mauclere, J. Lewis, and A. Gessain. 2002. Complete Sequence of a Novel Highly Divergent Simian T-Cell Lymphotropic Virus from Wild-Caught Red-Capped Mangabeys (Cercocebus torquatus) from Cameroon: a New Primate T-Lymphotropic Virus Type 3 Subtype. J. Virol. 76(1):259-268.

7. Sitbon, M., L. of Auriol, H. Ellerbrok, C. Andre, J. Nishio, S. Perryman, F. Pozo, S. F. Hayes, K. Wehrly, P. Tambourin, F. Galibert, and B. Chesebro. 1991. Substitution of leucine for isoleucine in a sequence highly conserved among retroviral envelope surface glycoproteins attenuates the lytic effect of the Friend murine leukaemia virus. Proc Natl Acad Sci USA. 88(13):5932-6.

The invention claimed is:

1. A method for implementing processes for detecting a strain of PTLV, said process comprising the steps of:

(a) amplifying a target nucleic acid in a biological sample capable of containing PTLVs with pairs of degenerate 5' and 3' oligonucleotides in the 5' and 3' orientation originating from the nucleotide sequences coding for the amino-terminal region of the surface component (SU) of the envelope proteins of the viruses of T lymphomas/leukaemias in primates, collected together under the designation PTLV, said viruses being designated HTLV in man and STLV in the monkey, wherein the amino-terminal region is a protein fragment delimited on the N-terminal side by an amino acid situated between positions 75 to 90, and on the C-terminal side by an amino acid situated between positions 130 to 145 of the envelope protein of the MT-2 strain of HTLV-1 represented by SEQ ID No: 43, or of the envelope protein of the NRA strain of RTLV-2 represented by SEQ ID NO: 45, or of the envelope protein of the strain of STLV-3 represented by SEQ ID NO: 47, or a virus carrying the sequences belonging to the SU of PTLVs, and (b) identifying the strain of PTLV contained in the biological sample by determining nucleotide fragments that have been amplified.

2. The method according to claim 1, wherein said strain of PTLV is selected from the group consisting of HTLV-1, HTLV-2, STLV-1, STLV-2, and STLV-3.

3. The method according to claim 1, wherein said degenerate oligonucleotides are chosen from those comprising approximately 15 to approximately 30 nucleotides originating from the nucleotide sequences coding for protein fragments delimited on the N-terminal side by an amino acid situated between positions 75 to 90, and on the C-terminal side by an amino acid situated between positions 130 to 145 of the envelope protein of the MT-2 strain of HTLV-1 represented by SEQ ID NO: 43, or of the envelope protein of the NRA strain of HTLV-2 represented by SEQ ID NO: 45, or of the envelope protein of the strain of STLV-3 represented by SEQ ID NO: 47, and wherein said degenerate oligonucleotides comprise a mixture of oligonucleotides originating from sequences coding for a determined region of approximately 5 to 10 amino acids of the envelope proteins of the different strains of PTLV, and which differ from each other by the substitution of at least one nucleotide by another in a manner such that each oligonucleotide is capable of coding for the abovementioned determined region originating from the protein fragments of the envelope proteins of the different strains of PTLVs.

4. The method according to claim 1, wherein pairs of degenerate oligonucleotides comprise approximately 15 to approximately 30 nucleotides originating from nucleotide sequences coding for polypeptide fragments of approximately 5 to approximately 10 amino acids originating from protein fragments delimited by the amino acids situated at positions 80 to 145, and more particularly at positions 83 to 145, of the envelope protein of the MT-2 strain of HTLV-1 represented by SEQ ID NO: 43.

5. The method according to claim 1, wherein the pairs of degenerate oligonucleotides originate from nucleotide sequences coding for the polypeptide fragment 83-88 represented by SEQ ID NO: 1, and polypeptide fragment 140-145 represented by SEQ ID NO: 2, of the envelope protein of the MT-2 strain of HTLV-1

6. The method according to claim 1, wherein the degenerate oligonucleotides are degenerate oligonucleoticles in 5' orientation originating from the DNA (+) strand coding for a polypeptide selected from the group consisting of:

a polypeptide fragment 83-88 of the envelope protein of the MT-2 strain of HTLV-1, said oligonucleotides being chosen from those of following formula (I): .

```
TAYBTNTTYCCNCAYTGG     (I)     SEQ ID NO: 5
```

in which:
Y represents C or T,
B represents C, G or T,
N represents A, C, G or T,
provided that when N represents T, B cannot represent T, and
a polypeptide fragment 140-145 of the envelope protein of the MT-2 strain of HTLV-1, said oligonucleotides being chosen from those of following formula (II):

```
AAYTTYACNCARGARGT      (II)    SEQ ID NO: 8
```

in which:
Y represents C or T,
R represents A or G,
N represents A. C, G or T.

7. The method according to claim 5, wherein the degenerate oligonucleotides are degenerate oligonucleotides in 3' orientation originating from the DNA (−) strand coding for the polypeptide fragment 140-145 of the envelope protein of the MT-2 strain of HTLV-1, and wherein said oligonucleotides are of formula (III):

```
NACYTCYTGNGTRAARTT     (III)    SEQ ID NO: 13
```

in which:
Y represents C or T,
R represents A or G,
N represents A, C, C or t.

8. The method according to claim 1, wherein the pairs of degenerate oligonucleotides are selected from the group consisting of:

a degenerate 5' oligonucleotide corresponding to a mixture of 5' oligonucleotides originating from a same determined nucleotide region comprising approximately 15 to approximately 30 nucleotides originating from the DNA (+) strand and coding for the polypeptide fragments of approximately 5 to approximately 10 amino acids originating from protein fragments delimited on the N-terminal side by an amino acid situated between positions 75 to 90, and on the C-terminal side by an amino acid situated between positions 135 to 150 of the envelope protein of the MT-2 strain of HTLV-1 represented by SEQ ID No: 43, or of the envelope protein of the NRA strain of HTLV-2 represented by SEQ ID NO: 45, or of the envelope protein of the strain of STLV-3 represented by SEQ ID NO: 47, said 5' oligonucleotides are different from each other by substitution of at least one nucleotide by another such that each oligonucleotide is capable of coding for the abovementioned determined region originating from protein fragments of the envelope proteins of different strains of PTLVs, and a degenerate 3' oligonucleotide corresponding to a mixture of 3' oligonucleotides originating from a same determined nucleotide region comprising approximately 15 to approximately 30 nucleotides originating from the DNA (−) strand and coding for the polypeptide fragments of approximately 5 to approximately 10 amino acids originating from protein fragments delimited on the N-terminal side by an amino acid situated between positions 125 to 145, and on the C-terminal side by an amino acid situated between positions 130 to 145 of the envelope protein of the MT-2 strain of HTLV-1 represented by SEQ ID No: 43, or of the envelope protein of the NRA strain of HTLV-2 represented by SEQ ID NO: 45, or of the envelope protein of the strain of STLV-3 represented by SEQ ID NO: 47, wherein said 3' oligonucleotides being such that they differ from each other by substitution of at least one nucleotide by another such that each oligonucleotide is capable of coding for the abovementioned determined region originating from the protein fragments of the envelope proteins of the different strains of PTLVs, and wherein said 5' and 3' primers cannot be complementary to each other.

9. The method according to claim 7, wherein the degenerate 5' oligonucleotides are selected from the group consisting of SEQ ID NO:5, SEQ ID NO:8 and SEQ ID NO:13.

10. The method according to claim 7, wherein the degenerate 5' oligonucleotides_encode for the protein fragments comprising a sequence delimited on the N-terminal side by the amino acid situated in position 89, and on the C-terminal side by the amino acid situated in position 139 of the envelope protein of the MT-2 strain of HTLV-1 represented by SEQ ID NO: 43, or a sequence comprising an envelope protein of a strain of PTLV other than HTLV-1, wherein the sequence delimited on the N- terminal side by the amino acid situated in position 85, and on the C-terminal side by the amino acid situated in position 135 of the envelope protein of the NRA strain of HTLV-2 represented by SEQ ID NO: 45, or a sequence delimited on the N-terminal side by the amino acid situated in position 88, and on the C-terminal side by the amino acid situated in position 144 of the envelope protein of the strain of STLV-3 represented by SEQ ID NO:47.

11. The method according to claim 10, wherein the degenerate 5' oligonucleotide is SEQ ID NO:5 or SEQ ID NO:13.

12. The method according to claim 10, wherein the degenerate 5' oligonucleotides are SEQ ID NO: 5 and SEQ ID NO: 14.

13. A process for detecting any strain of PTLV, as well as any strain of virus comprising the sequences belonging to the SU of PTLVs, said process comprising:

contacting a pair of degenerate 5' and 3' oligonucleotides encoding for peptides of SEQ ID NO: 1 and SEQ ID NO: 2 with genomic DNA or complementary DNA derived from a biological sample containing PTLV, amplifying DNA fragments of said genomic DNA or complementary DNA derived from a biological sample containing PTLV coding for a fragment of the envelope proteins of the different strains of PTLVs, and detecting the DNA fragments amplified during the previous stage to determine whether said sample contains said PTLV.

14. The process of claim 13, wherein said strains of PTLVS are selected from the group consisting of: HTLV-1, HTLV-2, STLV-1, STLV-2, and STLV-3.

15. A process for detecting a strain of PTLV comprising SEQ ID NO: 43, said process comprising:

contacting genomic DNA or complementary DNA derived from a biological sample containing said PTLV with a pair of degenerate 5' and 3' oligonucleotides encoding for peptides of SEQ ID NO: 1 and SEQ ID NO: 2, amplifying DNA fragments of said genomic DNA or complementary DNA derived from a biological sample containing PTLV, and detecting the DNA fragments amplified during the previous stage to determine whether said sample contains said PTLV.

* * * * *

SEQUENCE LISTING

```
<160> NUMBER OF SEQ ID NOS: 47

<210> SEQ ID NO 1
<211> LENGTH: 6
<212> TYPE: PRT
<213> ORGANISM: Human T-cell lymphotropic virus type 1
<220> FEATURE:
<221> NAME/KEY: misc_feature
<222> LOCATION: (2)..(2)
<223> OTHER INFORMATION: L or V

<400> SEQUENCE: 1
```

-continued

```
Tyr Xaa Phe Pro His Trp
1               5


<210> SEQ ID NO 2
<211> LENGTH: 6
<212> TYPE: PRT
<213> ORGANISM: Human T-cell lymphotropic virus type 1
<220> FEATURE:
<221> NAME/KEY: misc_feature
<222> LOCATION: (4)..(4)
<223> OTHER INFORMATION: Q or R

<400> SEQUENCE: 2

Asn Phe Thr Xaa Glu Val
1               5


<210> SEQ ID NO 3
<211> LENGTH: 7
<212> TYPE: PRT
<213> ORGANISM: Human T-cell lymphotropic virus type 1
<220> FEATURE:
<221> NAME/KEY: misc_feature
<222> LOCATION: (3)..(3)
<223> OTHER INFORMATION: S or T
<220> FEATURE:
<221> NAME/KEY: misc_feature
<222> LOCATION: (5)..(5)
<223> OTHER INFORMATION: I or M

<400> SEQUENCE: 3

Asn Tyr Xaa Cys Xaa Val Cys
1               5


<210> SEQ ID NO 4
<211> LENGTH: 5
<212> TYPE: PRT
<213> ORGANISM: Human T-cell lymphotropic virus type 1

<400> SEQUENCE: 4

Trp His Val Leu Tyr
1               5


<210> SEQ ID NO 5
<211> LENGTH: 18
<212> TYPE: DNA
<213> ORGANISM: artificial sequence
<220> FEATURE:
<223> OTHER INFORMATION: 5' oligonucl,otide from the  DNA (+) strand
      corresponding to the 83-88 polypeptide fragment
      of HTLV-1 strain MT-2 enveloppe protein
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (4)..(4)
<223> OTHER INFORMATION: C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: C or T
<220> FEATURE:
<221> NAME/KEY: misc_feature
<222> LOCATION: (12)..(12)
<223> OTHER INFORMATION: A, C, G or T
<220> FEATURE:
<221> NAME/KEY: misc_feature
```

-continued

<222> LOCATION: (15)..(15)
<223> OTHER INFORMATION: C or T

<400> SEQUENCE: 5
tanntnttnc cncantgg 18

<210> SEQ ID NO 6
<211> LENGTH: 18
<212> TYPE: DNA
<213> ORGANISM: artificial sequence
<220> FEATURE:
<223> OTHER INFORMATION: 5' oligonucl,otide from the DNA (+) strand corresponding to the 83-88 polypeptide fragment of HTLV-1 strain MT-2 enveloppe protein
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (4)..(4)
<223> OTHER INFORMATION: C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: C or T
<220> FEATURE:
<221> NAME/KEY: misc_feature
<222> LOCATION: (12)..(12)
<223> OTHER INFORMATION: A, C, G or T

<400> SEQUENCE: 6
tanntnttnc cncactgg 18

<210> SEQ ID NO 7
<211> LENGTH: 18
<212> TYPE: DNA
<213> ORGANISM: artificial sequence
<220> FEATURE:
<223> OTHER INFORMATION: 5' oligonucl,otide from the DNA (+) strand corresponding to the 83-88 polypeptide fragment of HTLV-1 strain MT-2 enveloppe protein
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (4)..(4)
<223> OTHER INFORMATION: C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: C or T
<220> FEATURE:
<221> NAME/KEY: misc_feature
<222> LOCATION: (12)..(12)
<223> OTHER INFORMATION: A, C, G or T

<400> SEQUENCE: 7
tanntnttnc cncattgg 18

<210> SEQ ID NO 8
<211> LENGTH: 17
<212> TYPE: DNA

-continued

```
<213> ORGANISM: artificial sequence
<220> FEATURE:
<223> OTHER INFORMATION: 5' oligonucl,otide from the  DNA (+) strand
      corresponding to the 140-145 polypeptide fragment
      of HTLV-1 strain MT-2 enveloppe protein
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (6)..(6)
<223> OTHER INFORMATION: C or T
<220> FEATURE:
<221> NAME/KEY: misc_feature
<222> LOCATION: (9)..(9)
<223> OTHER INFORMATION: A, C, G or T
<220> FEATURE:
<221> NAME/KEY: misc_feature
<222> LOCATION: (12)..(12)
<223> OTHER INFORMATION: A or G
<220> FEATURE:
<221> NAME/KEY: misc_feature
<222> LOCATION: (15)..(15)
<223> OTHER INFORMATION: A or G

<400> SEQUENCE: 8

aanttnacnc angangt                                                17


<210> SEQ ID NO 9
<211> LENGTH: 17
<212> TYPE: DNA
<213> ORGANISM: artificial sequence
<220> FEATURE:
<223> OTHER INFORMATION: 5' oligonucl,otide from the  DNA (+) strand
      corresponding to the 140-145 polypeptide fragment
      of HTLV-1 strain MT-2 enveloppe protein
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (6)..(6)
<223> OTHER INFORMATION: C or T
<220> FEATURE:
<221> NAME/KEY: misc_feature
<222> LOCATION: (9)..(9)
<223> OTHER INFORMATION: A, C, G or T

<400> SEQUENCE: 9

aanttnacnc aagaagt                                                17


<210> SEQ ID NO 10
<211> LENGTH: 17
<212> TYPE: DNA
<213> ORGANISM: artificial sequence
<220> FEATURE:
<223> OTHER INFORMATION: 5' oligonucl,otide from the  DNA (+) strand
      corresponding to the 140-145 polypeptide fragment
      of HTLV-1 strain MT-2 enveloppe protein
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (6)..(6)
<223> OTHER INFORMATION: C or T
<220> FEATURE:
<221> NAME/KEY: misc_feature
<222> LOCATION: (9)..(9)
<223> OTHER INFORMATION: A, C, G or T

<400> SEQUENCE: 10
```

-continued aanttnacnc aggaagt 17

<210> SEQ ID NO 11
<211> LENGTH: 17
<212> TYPE: DNA
<213> ORGANISM: artificial sequence
<220> FEATURE:
<223> OTHER INFORMATION: 5' oligonucl,otide from the DNA (+) strand
corresponding to the 140-145 polypeptide fragment
of HTLV-1 strain MT-2 enveloppe protein
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (6)..(6)
<223> OTHER INFORMATION: C or T
<220> FEATURE:
<221> NAME/KEY: misc_feature
<222> LOCATION: (9)..(9)
<223> OTHER INFORMATION: A, C, G or T

<400> SEQUENCE: 11
aanttnacnc aagaggt 17

<210> SEQ ID NO 12
<211> LENGTH: 17
<212> TYPE: DNA
<213> ORGANISM: artificial sequence
<220> FEATURE:
<223> OTHER INFORMATION: 5' oligonucl,otide from the DNA (+) strand
corresponding to the 140-145 polypeptide fragment
of HTLV-1 strain MT-2 enveloppe protein
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (6)..(6)
<223> OTHER INFORMATION: C or T
<220> FEATURE:
<221> NAME/KEY: misc_feature
<222> LOCATION: (9)..(9)
<223> OTHER INFORMATION: A, C, G or T

<400> SEQUENCE: 12
aanttnacnc aggaggt 17

<210> SEQ ID NO 13
<211> LENGTH: 18
<212> TYPE: DNA
<213> ORGANISM: artificial sequence
<220> FEATURE:
<223> OTHER INFORMATION: 3' oligonucl,otide from the DNA (-) strand
corresponding to the 140-145 polypeptide fragment
of HTLV-1 strain MT-2 enveloppe protein
<220> FEATURE:
<221> NAME/KEY: misc_feature
<222> LOCATION: (1)..(1)
<223> OTHER INFORMATION: A, C, G or T
<220> FEATURE:
<221> NAME/KEY: misc_feature
<222> LOCATION: (4)..(4)
<223> OTHER INFORMATION: C or T
<220> FEATURE:
<221> NAME/KEY: misc_feature
<222> LOCATION: (7)..(7)
<223> OTHER INFORMATION: C or T
<220> FEATURE:
<221> NAME/KEY: misc_feature
<222> LOCATION: (10)..(10)

-continued

<223> OTHER INFORMATION: A, C, G or T
<220> FEATURE:
<221> NAME/KEY: misc_feature
<222> LOCATION: (13)..(13)
<223> OTHER INFORMATION: A or G
<220> FEATURE:
<221> NAME/KEY: misc_feature
<222> LOCATION: (16)..(16)
<223> OTHER INFORMATION: A or G

<400> SEQUENCE: 13
nacntcntgn gtnaantt 18

<210> SEQ ID NO 14
<211> LENGTH: 18
<212> TYPE: DNA
<213> ORGANISM: artificial sequence
<220> FEATURE:
<223> OTHER INFORMATION: 3' oligonucl,otide from the DNA (-) strand corresponding to the 140-145 polypeptide fragment of HTLV-1 strain MT-2 enveloppe protein
<220> FEATURE:
<221> NAME/KEY: misc_feature
<222> LOCATION: (1)..(1)
<223> OTHER INFORMATION: A, C, G or T
<220> FEATURE:
<221> NAME/KEY: misc_feature
<222> LOCATION: (4)..(4)
<223> OTHER INFORMATION: C or T
<220> FEATURE:
<221> NAME/KEY: misc_feature
<222> LOCATION: (7)..(7)
<223> OTHER INFORMATION: C or T
<220> FEATURE:
<221> NAME/KEY: misc_feature
<222> LOCATION: (10)..(10)
<223> OTHER INFORMATION: A, C, G or T

<400> SEQUENCE: 14
nacntcntgn gtaaaatt 18

<210> SEQ ID NO 15
<211> LENGTH: 18
<212> TYPE: DNA
<213> ORGANISM: artificial sequence
<220> FEATURE:
<223> OTHER INFORMATION: 3' oligonucl,otide from the DNA (-) strand corresponding to the 140-145 polypeptide fragment of HTLV-1 strain MT-2 enveloppe protein
<220> FEATURE:
<221> NAME/KEY: misc_feature
<222> LOCATION: (1)..(1)
<223> OTHER INFORMATION: A, C, G or T
<220> FEATURE:
<221> NAME/KEY: misc_feature
<222> LOCATION: (4)..(4)
<223> OTHER INFORMATION: C or T
<220> FEATURE:
<221> NAME/KEY: misc_feature
<222> LOCATION: (7)..(7)
<223> OTHER INFORMATION: C or T
<220> FEATURE:
<221> NAME/KEY: misc_feature
<222> LOCATION: (10)..(10)
<223> OTHER INFORMATION: A, C, G or T

<400> SEQUENCE: 15
nacntcntgn gtgaaatt 18

<210> SEQ ID NO 16
<211> LENGTH: 18
<212> TYPE: DNA
<213> ORGANISM: artificial sequence -continued

```
<220> FEATURE:
<223> OTHER INFORMATION: 3' oligonucl,otide from the  DNA (-) strand
      corresponding to the 140-145 polypeptide fragment
      of HTLV-1 strain MT-2 enveloppe protein
<220> FEATURE:
<221> NAME/KEY: misc_feature
<222> LOCATION: (1)..(1)
<223> OTHER INFORMATION: A, C, G or T
<220> FEATURE:
<221> NAME/KEY: misc_feature
<222> LOCATION: (4)..(4)
<223> OTHER INFORMATION: C or T
<220> FEATURE:
<221> NAME/KEY: misc_feature
<222> LOCATION: (7)..(7)
<223> OTHER INFORMATION: C or T
<220> FEATURE:
<221> NAME/KEY: misc_feature
<222> LOCATION: (10)..(10)
<223> OTHER INFORMATION: A, C, G or T

<400> SEQUENCE: 16

nacntcntgn gtaaagtt                                                  18


<210> SEQ ID NO 17
<211> LENGTH: 18
<212> TYPE: DNA
<213> ORGANISM: artificial sequence
<220> FEATURE:
<223> OTHER INFORMATION: 3' oligonucl,otide from the  DNA (-) strand
      corresponding to the 140-145 polypeptide fragment
      of HTLV-1 strain MT-2 enveloppe protein
<220> FEATURE:
<221> NAME/KEY: misc_feature
<222> LOCATION: (1)..(1)
<223> OTHER INFORMATION: A, C, G or T
<220> FEATURE:
<221> NAME/KEY: misc_feature
<222> LOCATION: (4)..(4)
<223> OTHER INFORMATION: C or T
<220> FEATURE:
<221> NAME/KEY: misc_feature
<222> LOCATION: (7)..(7)
<223> OTHER INFORMATION: C or T
<220> FEATURE:
<221> NAME/KEY: misc_feature
<222> LOCATION: (10)..(10)
<223> OTHER INFORMATION: A, C, G or T

<400> SEQUENCE: 17

nacntcntgn gtgaagtt                                                  18


<210> SEQ ID NO 18
<211> LENGTH: 20
<212> TYPE: DNA
<213> ORGANISM: artificial sequence
<220> FEATURE:
<223> OTHER INFORMATION: 3' oligonucl,otide from the  DNA (-) strand
      corresponding to the 222-228 polypeptide fragment
      of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (2)..(2)
<223> OTHER INFORMATION: A or C
<220> FEATURE:
<221> NAME/KEY: misc_feature
<222> LOCATION: (3)..(3)
<223> OTHER INFORMATION: A, C, G or T
<220> FEATURE:
<221> NAME/KEY: misc_feature
<222> LOCATION: (6)..(6)
```

-continued

<223> OTHER INFORMATION: A, C, G or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: A, C, G or T
<220> FEATURE:
<221> NAME/KEY: misc_feature
<222> LOCATION: (13)..(13)
<223> OTHER INFORMATION: C or G
<220> FEATURE:
<221> NAME/KEY: misc_feature
<222> LOCATION: (14)..(14)
<223> OTHER INFORMATION: A or T
<220> FEATURE:
<221> NAME/KEY: misc_feature
<222> LOCATION: (15)..(15)
<223> OTHER INFORMATION: A or G
<220> FEATURE:
<221> NAME/KEY: misc_feature
<222> LOCATION: (18)..(18)
<223> OTHER INFORMATION: A or G

<400> SEQUENCE: 18
nnnacnatnc annwntantt 20

<210> SEQ ID NO 19
<211> LENGTH: 20
<212> TYPE: DNA
<213> ORGANISM: artificial sequence
<220> FEATURE:
<223> OTHER INFORMATION: 3' oligonucl,otide from the DNA (-) strand
corresponding to the 222-228 polypeptide fragment
of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (2)..(2)
<223> OTHER INFORMATION: A or C
<220> FEATURE:
<221> NAME/KEY: misc_feature
<222> LOCATION: (3)..(3)
<223> OTHER INFORMATION: A, C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: A, C, G or T
<220> FEATURE:
<221> NAME/KEY: misc_feature
<222> LOCATION: (13)..(13)
<223> OTHER INFORMATION: C or G

<400> SEQUENCE: 19
nnnacnatnc annaataatt 20

<210> SEQ ID NO 20
<211> LENGTH: 20
<212> TYPE: DNA
<213> ORGANISM: artificial sequence
<220> FEATURE:
<223> OTHER INFORMATION: 3' oligonucl,otide from the DNA (-) strand -continued

```
      corresponding to the 222-228 polypeptide fragment
      of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (2)..(2)
<223> OTHER INFORMATION: A or C
<220> FEATURE:
<221> NAME/KEY: misc_feature
<222> LOCATION: (3)..(3)
<223> OTHER INFORMATION: A, C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: A, C, G or T
<220> FEATURE:
<221> NAME/KEY: misc_feature
<222> LOCATION: (13)..(13)
<223> OTHER INFORMATION: C or G

<400> SEQUENCE: 20

nnnacnatnc annagtaatt                                                  20


<210> SEQ ID NO 21
<211> LENGTH: 20
<212> TYPE: DNA
<213> ORGANISM: artificial sequence
<220> FEATURE:
<223> OTHER INFORMATION: 3' oligonucl,otide from the  DNA (-) strand
      corresponding to the 222-228 polypeptide fragment
      of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (2)..(2)
<223> OTHER INFORMATION: A or C
<220> FEATURE:
<221> NAME/KEY: misc_feature
<222> LOCATION: (3)..(3)
<223> OTHER INFORMATION: A, C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: A, C, G or T
<220> FEATURE:
<221> NAME/KEY: misc_feature
<222> LOCATION: (13)..(13)
<223> OTHER INFORMATION: C or G

<400> SEQUENCE: 21

nnnacnatnc annaatagtt                                                  20


<210> SEQ ID NO 22
```

-continued

<211> LENGTH: 20
<212> TYPE: DNA
<213> ORGANISM: artificial sequence
<220> FEATURE:
<223> OTHER INFORMATION: 3' oligonucl,otide from the DNA (-) strand
corresponding to the 222-228 polypeptide fragment
of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (2)..(2)
<223> OTHER INFORMATION: A or C
<220> FEATURE:
<221> NAME/KEY: misc_feature
<222> LOCATION: (3)..(3)
<223> OTHER INFORMATION: A, C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: A, C, G or T
<220> FEATURE:
<221> NAME/KEY: misc_feature
<222> LOCATION: (13)..(13)
<223> OTHER INFORMATION: C or G

<400> SEQUENCE: 22
nnnacnatnc annagtagtt 20

<210> SEQ ID NO 23
<211> LENGTH: 20
<212> TYPE: DNA
<213> ORGANISM: artificial sequence
<220> FEATURE:
<223> OTHER INFORMATION: 3' oligonucl,otide from the DNA (-) strand
corresponding to the 222-228 polypeptide fragment
of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (2)..(2)
<223> OTHER INFORMATION: A or C
<220> FEATURE:
<221> NAME/KEY: misc_feature
<222> LOCATION: (3)..(3)
<223> OTHER INFORMATION: A, C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: A, C, G or T
<220> FEATURE:
<221> NAME/KEY: misc_feature
<222> LOCATION: (13)..(13)
<223> OTHER INFORMATION: C or G

<400> SEQUENCE: 23

```
nnnacnatnc anntataatt                                              20


<210> SEQ ID NO 24
<211> LENGTH: 20
<212> TYPE: DNA
<213> ORGANISM: artificial sequence
<220> FEATURE:
<223> OTHER INFORMATION: 3' oligonucl,otide from the  DNA (-) strand
      corresponding to the 222-228 polypeptide fragment
      of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (2)..(2)
<223> OTHER INFORMATION: A or C
<220> FEATURE:
<221> NAME/KEY: misc_feature
<222> LOCATION: (3)..(3)
<223> OTHER INFORMATION: A, C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: A, C, G or T
<220> FEATURE:
<221> NAME/KEY: misc_feature
<222> LOCATION: (13)..(13)
<223> OTHER INFORMATION: C or G

<400> SEQUENCE: 24

nnnacnatnc anntgtaatt                                              20


<210> SEQ ID NO 25
<211> LENGTH: 20
<212> TYPE: DNA
<213> ORGANISM: artificial sequence
<220> FEATURE:
<223> OTHER INFORMATION: 3' oligonucl,otide from the  DNA (-) strand
      corresponding to the 222-228 polypeptide fragment
      of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (2)..(2)
<223> OTHER INFORMATION: A or C
<220> FEATURE:
<221> NAME/KEY: misc_feature
<222> LOCATION: (3)..(3)
<223> OTHER INFORMATION: A, C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: A, C, G or T
<220> FEATURE:
```

-continued

<221> NAME/KEY: misc_feature
<222> LOCATION: (13)..(13)
<223> OTHER INFORMATION: C or G

<400> SEQUENCE: 25
nnnacnatnc anntatagtt 20

<210> SEQ ID NO 26
<211> LENGTH: 20
<212> TYPE: DNA
<213> ORGANISM: artificial sequence
<220> FEATURE:
<223> OTHER INFORMATION: 3' oligonucl,otide from the DNA (-) strand corresponding to the 222-228 polypeptide fragment of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (2)..(2)
<223> OTHER INFORMATION: A or C
<220> FEATURE:
<221> NAME/KEY: misc_feature
<222> LOCATION: (3)..(3)
<223> OTHER INFORMATION: A, C, G or T
<220> FEATURE:
<221> NAME/KEY: misc_feature
<222> LOCATION: (6)..(6)
<223> OTHER INFORMATION: A, C, G or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: A, C, G or T
<220> FEATURE:
<221> NAME/KEY: misc_feature
<222> LOCATION: (13)..(13)
<223> OTHER INFORMATION: C or G

<400> SEQUENCE: 26
nnnacnatnc anntgtagtt 20

<210> SEQ ID NO 27
<211> LENGTH: 15
<212> TYPE: DNA
<213> ORGANISM: artificial sequence
<220> FEATURE:
<223> OTHER INFORMATION: 3' oligonucl,otide from the DNA (-) strand corresponding to the 237-241 polypeptide fragment of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (4)..(4)
<223> OTHER INFORMATION: A, C, G or T
<220> FEATURE:
<221> NAME/KEY: misc_feature
<222> LOCATION: (6)..(6)
<223> OTHER INFORMATION: A or G
<220> FEATURE:
<221> NAME/KEY: misc_feature
<222> LOCATION: (7)..(7)
<223> OTHER INFORMATION: A, C, G or T
<220> FEATURE:
<221> NAME/KEY: misc_feature
<222> LOCATION: (10)..(10)
<223> OTHER INFORMATION: A or G -continued

<400> SEQUENCE: 27
ntanannacn tgcca 15

<210> SEQ ID NO 28
<211> LENGTH: 15
<212> TYPE: DNA
<213> ORGANISM: artificial sequence
<220> FEATURE:
<223> OTHER INFORMATION: 3' oligonucl,otide from the DNA (-) strand
corresponding to the 237-241 polypeptide fragment
of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (4)..(4)
<223> OTHER INFORMATION: A, C, G or T
<220> FEATURE:
<221> NAME/KEY: misc_feature
<222> LOCATION: (6)..(6)
<223> OTHER INFORMATION: A or G
<220> FEATURE:
<221> NAME/KEY: misc_feature
<222> LOCATION: (7)..(7)
<223> OTHER INFORMATION: A, C, G or T

<400> SEQUENCE: 28
ntanannaca tgcca 15

<210> SEQ ID NO 29
<211> LENGTH: 15
<212> TYPE: DNA
<213> ORGANISM: artificial sequence
<220> FEATURE:
<223> OTHER INFORMATION: 3' oligonucl,otide from the DNA (-) strand
corresponding to the 237-241 polypeptide fragment
of HTLV-1 strain MT-2 enveloppe protein
<220> FEATURE:
<221> NAME/KEY: misc_feature
<222> LOCATION: (1)..(1)
<223> OTHER INFORMATION: A or G
<220> FEATURE:
<221> NAME/KEY: misc_feature
<222> LOCATION: (4)..(4)
<223> OTHER INFORMATION: A, C, G or T
<220> FEATURE:
<221> NAME/KEY: misc_feature
<222> LOCATION: (6)..(6)
<223> OTHER INFORMATION: A or G
<220> FEATURE:
<221> NAME/KEY: misc_feature
<222> LOCATION: (7)..(7)
<223> OTHER INFORMATION: A, C, G or T

<400> SEQUENCE: 29
ntanannacg tgcca 15

<210> SEQ ID NO 30
<211> LENGTH: 153
<212> TYPE: DNA
<213> ORGANISM: Human T-cell lymphotropic virus type 1
<220> FEATURE:
<221> NAME/KEY: CDS
<222> LOCATION: (1)..(153)
<223> OTHER INFORMATION:

<400> SEQUENCE: 30 att aaa aag cca aac cca aat ggc gga ggc tat tat tta gcc tct tat 48
Ile Lys Lys Pro Asn Pro Asn Gly Gly Gly Tyr Tyr Leu Ala Ser Tyr -continued

```
1               5                   10                  15

tca gac cct tgt tcc tta aaa tgc cca tac ctg ggg tgc caa tca tgg        96
Ser Asp Pro Cys Ser Leu Lys Cys Pro Tyr Leu Gly Cys Gln Ser Trp
            20                  25                  30

acc tgc ccc tat aca gga gcc gtc tcc agc ccc tac tgg aag ttt cag       144
Thr Cys Pro Tyr Thr Gly Ala Val Ser Ser Pro Tyr Trp Lys Phe Gln
        35                  40                  45

caa gat gtc                                                           153
Gln Asp Val
    50


<210> SEQ ID NO 31
<211> LENGTH: 51
<212> TYPE: PRT
<213> ORGANISM: Human T-cell lymphotropic virus type 1

<400> SEQUENCE: 31

Ile Lys Lys Pro Asn Pro Asn Gly Gly Gly Tyr Tyr Leu Ala Ser Tyr
1               5                   10                  15

Ser Asp Pro Cys Ser Leu Lys Cys Pro Tyr Leu Gly Cys Gln Ser Trp
            20                  25                  30

Thr Cys Pro Tyr Thr Gly Ala Val Ser Ser Pro Tyr Trp Lys Phe Gln
        35                  40                  45

Gln Asp Val
    50


<210> SEQ ID NO 32
<211> LENGTH: 153
<212> TYPE: DNA
<213> ORGANISM: Human T-cell lymphotropic virus type 1
<220> FEATURE:
<221> NAME/KEY: CDS
<222> LOCATION: (1)..(153)
<223> OTHER INFORMATION:

<400> SEQUENCE: 32

gtt aaa aag cca aac cga aat ggc gga ggc tat tat tta gcc tct tat        48
Val Lys Lys Pro Asn Arg Asn Gly Gly Gly Tyr Tyr Leu Ala Ser Tyr
1               5                   10                  15

tca gac cct tgt tcc tta aaa tgc cca tac ctg ggg tgc caa tca tgg        96
Ser Asp Pro Cys Ser Leu Lys Cys Pro Tyr Leu Gly Cys Gln Ser Trp
            20                  25                  30

acc tgc ccc tat aca gga gcc gtc tcc agc ccc tac tgg aag ttt cag       144
Thr Cys Pro Tyr Thr Gly Ala Val Ser Ser Pro Tyr Trp Lys Phe Gln
        35                  40                  45

caa gat gtc                                                           153
Gln Asp Val
    50


<210> SEQ ID NO 33
<211> LENGTH: 51
<212> TYPE: PRT
<213> ORGANISM: Human T-cell lymphotropic virus type 1

<400> SEQUENCE: 33

Val Lys Lys Pro Asn Arg Asn Gly Gly Gly Tyr Tyr Leu Ala Ser Tyr
1               5                   10                  15

Ser Asp Pro Cys Ser Leu Lys Cys Pro Tyr Leu Gly Cys Gln Ser Trp
            20                  25                  30

Thr Cys Pro Tyr Thr Gly Ala Val Ser Ser Pro Tyr Trp Lys Phe Gln
        35                  40                  45
```

-continued

```
Gln Asp Val
    50


<210> SEQ ID NO 34
<211> LENGTH: 153
<212> TYPE: DNA
<213> ORGANISM: Human T-cell lymphotropic virus type 1
<220> FEATURE:
<221> NAME/KEY: CDS
<222> LOCATION: (1)..(153)
<223> OTHER INFORMATION:

<400> SEQUENCE: 34

att aaa aag cca aac cga aat ggc gga ggc tat tat tta gcc tct tat       48
Ile Lys Lys Pro Asn Arg Asn Gly Gly Gly Tyr Tyr Leu Ala Ser Tyr
1               5                   10                  15

tca gac cct tgt tcc tta aaa tgc cca tac ctg ggg tgc caa tca tgg       96
Ser Asp Pro Cys Ser Leu Lys Cys Pro Tyr Leu Gly Cys Gln Ser Trp
            20                  25                  30

acc tgc ccc tat aca gga gcc gtc tcc agc ccc tac tgg aag ttt caa      144
Thr Cys Pro Tyr Thr Gly Ala Val Ser Ser Pro Tyr Trp Lys Phe Gln
        35                  40                  45

caa gat gtc                                                          153
Gln Asp Val
    50


<210> SEQ ID NO 35
<211> LENGTH: 51
<212> TYPE: PRT
<213> ORGANISM: Human T-cell lymphotropic virus type 1

<400> SEQUENCE: 35

Ile Lys Lys Pro Asn Arg Asn Gly Gly Gly Tyr Tyr Leu Ala Ser Tyr
1               5                   10                  15

Ser Asp Pro Cys Ser Leu Lys Cys Pro Tyr Leu Gly Cys Gln Ser Trp
            20                  25                  30

Thr Cys Pro Tyr Thr Gly Ala Val Ser Ser Pro Tyr Trp Lys Phe Gln
        35                  40                  45

Gln Asp Val
    50


<210> SEQ ID NO 36
<211> LENGTH: 153
<212> TYPE: DNA
<213> ORGANISM: Human T-cell lymphotropic virus type 1
<220> FEATURE:
<221> NAME/KEY: CDS
<222> LOCATION: (1)..(153)
<223> OTHER INFORMATION:

<400> SEQUENCE: 36

gtt aaa aag cca aac cga aat ggc gga ggc tat tat tta gcc tct tat       48
Val Lys Lys Pro Asn Arg Asn Gly Gly Gly Tyr Tyr Leu Ala Ser Tyr
1               5                   10                  15

tca gac cct tgt tcc tta aaa tgc cca tac ctg ggg tgc caa tca tgg       96
Ser Asp Pro Cys Ser Leu Lys Cys Pro Tyr Leu Gly Cys Gln Ser Trp
            20                  25                  30

acc tgc ccc tat aca gga ccc gtc tcc agc ccc tac tgg aag ttt cag      144
Thr Cys Pro Tyr Thr Gly Pro Val Ser Ser Pro Tyr Trp Lys Phe Gln
        35                  40                  45

caa gat gtc                                                          153
Gln Asp Val
    50
```

-continued

```
<210> SEQ ID NO 37
<211> LENGTH: 51
<212> TYPE: PRT
<213> ORGANISM: Human T-cell lymphotropic virus type 1

<400> SEQUENCE: 37

Val Lys Lys Pro Asn Arg Asn Gly Gly Gly Tyr Tyr Leu Ala Ser Tyr
1               5                   10                  15

Ser Asp Pro Cys Ser Leu Lys Cys Pro Tyr Leu Gly Cys Gln Ser Trp
            20                  25                  30

Thr Cys Pro Tyr Thr Gly Pro Val Ser Ser Pro Tyr Trp Lys Phe Gln
        35                  40                  45

Gln Asp Val
    50


<210> SEQ ID NO 38
<211> LENGTH: 171
<212> TYPE: DNA
<213> ORGANISM: Human T-cell lymphotropic virus type 1
<220> FEATURE:
<221> NAME/KEY: CDS
<222> LOCATION: (1)..(171)
<223> OTHER INFORMATION:

<400> SEQUENCE: 38

att aaa aag cca aac cga aat ggc gga ggc tat cat tca gcc tct tat       48
Ile Lys Lys Pro Asn Arg Asn Gly Gly Gly Tyr His Ser Ala Ser Tyr
1               5                   10                  15

tca gac cct tgt tcc tta aag tgc cca tac ctg ggg tgc caa tca tgg       96
Ser Asp Pro Cys Ser Leu Lys Cys Pro Tyr Leu Gly Cys Gln Ser Trp
            20                  25                  30

acc tgc ccc tat gca gga gcc gtc tcc agc ccc tac tgg aag ttt cag      144
Thr Cys Pro Tyr Ala Gly Ala Val Ser Ser Pro Tyr Trp Lys Phe Gln
        35                  40                  45

caa gat gtc aat ttt acc cag gaa gta                                  171
Gln Asp Val Asn Phe Thr Gln Glu Val
    50                  55


<210> SEQ ID NO 39
<211> LENGTH: 57
<212> TYPE: PRT
<213> ORGANISM: Human T-cell lymphotropic virus type 1

<400> SEQUENCE: 39

Ile Lys Lys Pro Asn Arg Asn Gly Gly Gly Tyr His Ser Ala Ser Tyr
1               5                   10                  15

Ser Asp Pro Cys Ser Leu Lys Cys Pro Tyr Leu Gly Cys Gln Ser Trp
            20                  25                  30

Thr Cys Pro Tyr Ala Gly Ala Val Ser Ser Pro Tyr Trp Lys Phe Gln
        35                  40                  45

Gln Asp Val Asn Phe Thr Gln Glu Val
    50                  55


<210> SEQ ID NO 40
<211> LENGTH: 153
<212> TYPE: DNA
<213> ORGANISM: Human T-cell lymphotropic virus type 2
<220> FEATURE:
<221> NAME/KEY: CDS
<222> LOCATION: (1)..(153)
<223> OTHER INFORMATION:

<400> SEQUENCE: 40
```

-continued

```
ata aga aag cca aac aga cag ggc cta ggg tac tac tcg cct tcc tac       48
Ile Arg Lys Pro Asn Arg Gln Gly Leu Gly Tyr Tyr Ser Pro Ser Tyr
1               5                   10                  15

aat gac cct tgc tcg cta caa tgc ccc tac ttg ggc tcc caa tca tgg       96
Asn Asp Pro Cys Ser Leu Gln Cys Pro Tyr Leu Gly Ser Gln Ser Trp
            20                  25                  30

aca tgc cca tac acg gcc ccc gtc tcc act cca tcc tgg aat ttt cat      144
Thr Cys Pro Tyr Thr Ala Pro Val Ser Thr Pro Ser Trp Asn Phe His
        35                  40                  45

tca gat gta                                                          153
Ser Asp Val
    50
```

<210> SEQ ID NO 41
<211> LENGTH: 51
<212> TYPE: PRT
<213> ORGANISM: Human T-cell lymphotropic virus type 2

<400> SEQUENCE: 41

```
Ile Arg Lys Pro Asn Arg Gln Gly Leu Gly Tyr Tyr Ser Pro Ser Tyr
1               5                   10                  15

Asn Asp Pro Cys Ser Leu Gln Cys Pro Tyr Leu Gly Ser Gln Ser Trp
            20                  25                  30

Thr Cys Pro Tyr Thr Ala Pro Val Ser Thr Pro Ser Trp Asn Phe His
        35                  40                  45

Ser Asp Val
    50
```

<210> SEQ ID NO 42
<211> LENGTH: 924
<212> TYPE: DNA
<213> ORGANISM: Human T-cell lymphotropic virus type 1
<220> FEATURE:
<221> NAME/KEY: CDS
<222> LOCATION: (1)..(924)
<223> OTHER INFORMATION:

<400> SEQUENCE: 42

```
atg ggt aag ttt ctc gcc act ttg att tta ttc ttc cag ttc tgc ccc       48
Met Gly Lys Phe Leu Ala Thr Leu Ile Leu Phe Phe Gln Phe Cys Pro
1               5                   10                  15

ctc atc ctc ggt gat tac agc ccc agc tgc tgt act ctc aca att gga       96
Leu Ile Leu Gly Asp Tyr Ser Pro Ser Cys Cys Thr Leu Thr Ile Gly
            20                  25                  30

gtc tcc tca tac cac tct aaa ccc tgc aat cct gcc cag cca gtt tgt      144
Val Ser Ser Tyr His Ser Lys Pro Cys Asn Pro Ala Gln Pro Val Cys
        35                  40                  45

tcg tgg acc ctc gac ctg ctg gcc ctt tca gcg gat cag gcc cta cag      192
Ser Trp Thr Leu Asp Leu Leu Ala Leu Ser Ala Asp Gln Ala Leu Gln
    50                  55                  60

ccc ccc tgc cct aat cta gta agt tac tcc agc tac cat gcc acc tat      240
Pro Pro Cys Pro Asn Leu Val Ser Tyr Ser Ser Tyr His Ala Thr Tyr
65                  70                  75                  80

tcc cta tat cta ttc cct cat tgg att aaa aag cca aac cga aat ggc      288
Ser Leu Tyr Leu Phe Pro His Trp Ile Lys Lys Pro Asn Arg Asn Gly
                85                  90                  95

gga ggc tat tat tca gcc tct tat tca gac cct tgt tcc tta aag tgc      336
Gly Gly Tyr Tyr Ser Ala Ser Tyr Ser Asp Pro Cys Ser Leu Lys Cys
            100                 105                 110

cca tac ctg ggg tgc caa tca tgg acc tgc ccc tat aca gga gcc gtc      384
Pro Tyr Leu Gly Cys Gln Ser Trp Thr Cys Pro Tyr Thr Gly Ala Val
```

-continued

```
        115                 120                 125

tcc agc ccc tac tgg aag ttt cag caa gat gtc aat ttt act caa gaa      432
Ser Ser Pro Tyr Trp Lys Phe Gln Gln Asp Val Asn Phe Thr Gln Glu
    130                 135                 140

gtt tca cgc ctc aat att aat ctc cat ttt tca aaa tgc ggt ttt ccc      480
Val Ser Arg Leu Asn Ile Asn Leu His Phe Ser Lys Cys Gly Phe Pro
145                 150                 155                 160

ttc tcc ctt cta gtc gac gct cca gga tat gac ccc atc tgg ttc ctt      528
Phe Ser Leu Leu Val Asp Ala Pro Gly Tyr Asp Pro Ile Trp Phe Leu
                165                 170                 175

aat acc gaa ccc agc caa ctg cct ccc acc gcc cct cct cta ctc ccc      576
Asn Thr Glu Pro Ser Gln Leu Pro Pro Thr Ala Pro Pro Leu Leu Pro
            180                 185                 190

cac tct aac cta gac cac atc ctc gag ccc tct ata cca tgg aaa tca      624
His Ser Asn Leu Asp His Ile Leu Glu Pro Ser Ile Pro Trp Lys Ser
        195                 200                 205

aaa ctc ctg acc ctt gtc cag tta acc cta caa agc act aat tat act      672
Lys Leu Leu Thr Leu Val Gln Leu Thr Leu Gln Ser Thr Asn Tyr Thr
    210                 215                 220

tgc att gtc tgt atc gat cgt gcc agc cta tcc act tgg cac gtc cta      720
Cys Ile Val Cys Ile Asp Arg Ala Ser Leu Ser Thr Trp His Val Leu
225                 230                 235                 240

tac tct ccc aac gtc tct gtt cca tcc tct tct tct acc ccc ctc ctt      768
Tyr Ser Pro Asn Val Ser Val Pro Ser Ser Ser Ser Thr Pro Leu Leu
                245                 250                 255

tac cca tcg tta gcg ctt cca gcc ccc cac ctg acg tta cca ttt aac      816
Tyr Pro Ser Leu Ala Leu Pro Ala Pro His Leu Thr Leu Pro Phe Asn
            260                 265                 270

tgg acc cac tgc ttt gac ccc cag att caa gct ata gtc tcc tcc ccc      864
Trp Thr His Cys Phe Asp Pro Gln Ile Gln Ala Ile Val Ser Ser Pro
        275                 280                 285

tgt cat aac tcc ctc atc ctg ccc ccc ttt tcc ttg tca cct gtt ccc      912
Cys His Asn Ser Leu Ile Leu Pro Pro Phe Ser Leu Ser Pro Val Pro
    290                 295                 300

acc cta gga tcc                                                      924
Thr Leu Gly Ser
305


<210> SEQ ID NO 43
<211> LENGTH: 308
<212> TYPE: PRT
<213> ORGANISM: Human T-cell lymphotropic virus type 1

<400> SEQUENCE: 43

Met Gly Lys Phe Leu Ala Thr Leu Ile Leu Phe Phe Gln Phe Cys Pro
1               5                   10                  15

Leu Ile Leu Gly Asp Tyr Ser Pro Ser Cys Cys Thr Leu Thr Ile Gly
            20                  25                  30

Val Ser Ser Tyr His Ser Lys Pro Cys Asn Pro Ala Gln Pro Val Cys
        35                  40                  45

Ser Trp Thr Leu Asp Leu Leu Ala Leu Ser Ala Asp Gln Ala Leu Gln
    50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Ile Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110
```

-continued

Pro Tyr Leu Gly Cys Gln Ser Trp Thr Cys Pro Tyr Thr Gly Ala Val
115 120 125

Ser Ser Pro Tyr Trp Lys Phe Gln Gln Asp Val Asn Phe Thr Gln Glu
130 135 140

Val Ser Arg Leu Asn Ile Asn Leu His Phe Ser Lys Cys Gly Phe Pro
145 150 155 160

Phe Ser Leu Leu Val Asp Ala Pro Gly Tyr Asp Pro Ile Trp Phe Leu
165 170 175

Asn Thr Glu Pro Ser Gln Leu Pro Pro Thr Ala Pro Pro Leu Leu Pro
180 185 190

His Ser Asn Leu Asp His Ile Leu Glu Pro Ser Ile Pro Trp Lys Ser
195 200 205

Lys Leu Leu Thr Leu Val Gln Leu Thr Leu Gln Ser Thr Asn Tyr Thr
210 215 220

Cys Ile Val Cys Ile Asp Arg Ala Ser Leu Ser Thr Trp His Val Leu
225 230 235 240

Tyr Ser Pro Asn Val Ser Val Pro Ser Ser Ser Ser Thr Pro Leu Leu
245 250 255

Tyr Pro Ser Leu Ala Leu Pro Ala Pro His Leu Thr Leu Pro Phe Asn
260 265 270

Trp Thr His Cys Phe Asp Pro Gln Ile Gln Ala Ile Val Ser Ser Pro
275 280 285

Cys His Asn Ser Leu Ile Leu Pro Pro Phe Ser Leu Ser Pro Val Pro
290 295 300

Thr Leu Gly Ser
305

<210> SEQ ID NO 44
<211> LENGTH: 912
<212> TYPE: DNA
<213> ORGANISM: Human T-cell lymphotropic virus type 2
<220> FEATURE:
<221> NAME/KEY: CDS
<222> LOCATION: (1)..(912)
<223> OTHER INFORMATION:

<400> SEQUENCE: 44 atg ggt aac gtt ttc ttc cta ctt tta ttc agt ctc aca cac ttc cca 48
Met Gly Asn Val Phe Phe Leu Leu Leu Phe Ser Leu Thr His Phe Pro
1 5 10 15 cca gtc cag cag agc cga tgc aca ctc acg gtt ggt att tcc tcc tac 96
Pro Val Gln Gln Ser Arg Cys Thr Leu Thr Val Gly Ile Ser Ser Tyr
20 25 30 cac tcc agc ccc tgt agc cca acc caa ccc gtc tgc acg tgg aac ctc 144
His Ser Ser Pro Cys Ser Pro Thr Gln Pro Val Cys Thr Trp Asn Leu
35 40 45 gac ctt aat tcc cta acg acg gac cag cga cta cat ccc ccc tgc cct 192
Asp Leu Asn Ser Leu Thr Thr Asp Gln Arg Leu His Pro Pro Cys Pro
50 55 60 aac cta att act tac tct ggc ttc cac aaa act tat tcc tta tac tta 240
Asn Leu Ile Thr Tyr Ser Gly Phe His Lys Thr Tyr Ser Leu Tyr Leu
65 70 75 80 ttc cca cat tgg ata aag aag cca aat aga cag ggc cta gga tac tac 288
Phe Pro His Trp Ile Lys Lys Pro Asn Arg Gln Gly Leu Gly Tyr Tyr
85 90 95 tcg ccc tcc tat aat gac cct tgc tcg cta caa tgc ccc tac tta ggc 336
Ser Pro Ser Tyr Asn Asp Pro Cys Ser Leu Gln Cys Pro Tyr Leu Gly
100 105 110

-continued

```
tgc caa tca tgg aca tgc cca tac acg ggc ccc gtc tcc agt cca tcc      384
Cys Gln Ser Trp Thr Cys Pro Tyr Thr Gly Pro Val Ser Ser Pro Ser
        115                 120                 125

tgg aag ttt cac tca gat gta aat ttc acc caa gaa gtc agc caa gtg      432
Trp Lys Phe His Ser Asp Val Asn Phe Thr Gln Glu Val Ser Gln Val
    130                 135                 140

tcc ctt cga cta cac ttc tct aag tgc ggc tcc tcc atg acc ctt cta      480
Ser Leu Arg Leu His Phe Ser Lys Cys Gly Ser Ser Met Thr Leu Leu
145                 150                 155                 160

gta gat gcc cct gga tat gat cct tta tgg ttc atc acc tca gaa ccc      528
Val Asp Ala Pro Gly Tyr Asp Pro Leu Trp Phe Ile Thr Ser Glu Pro
                165                 170                 175

act cag cct ccc cca act cct ccc cca ctg gtc cat gac tcc gac ctt      576
Thr Gln Pro Pro Pro Thr Pro Pro Pro Leu Val His Asp Ser Asp Leu
            180                 185                 190

gaa cac gtc cta acc ccc tcc acg tct tgg aca acc aaa atg ctc aag      624
Glu His Val Leu Thr Pro Ser Thr Ser Trp Thr Thr Lys Met Leu Lys
        195                 200                 205

ttt atc cag ctg acc ttg cag agc acc aat tac tcc tgc atg gtt tgc      672
Phe Ile Gln Leu Thr Leu Gln Ser Thr Asn Tyr Ser Cys Met Val Cys
    210                 215                 220

gtg gat aga tcc agc ctc tca tcc tgg cat gtg ctc tac acc ccc aac      720
Val Asp Arg Ser Ser Leu Ser Ser Trp His Val Leu Tyr Thr Pro Asn
225                 230                 235                 240

atc tcc att ccc caa caa acc tcc tcc cga acc atc ctc ttt cct tct      768
Ile Ser Ile Pro Gln Gln Thr Ser Ser Arg Thr Ile Leu Phe Pro Ser
                245                 250                 255

ctt gcc ctg ccc gct cct cca ttc caa ccc ttc cct tgg acc cat tgc      816
Leu Ala Leu Pro Ala Pro Pro Phe Gln Pro Phe Pro Trp Thr His Cys
            260                 265                 270

tac caa cct cgc cta cag gca ata acg aca gat gac tgc aac aac tcc      864
Tyr Gln Pro Arg Leu Gln Ala Ile Thr Thr Asp Asp Cys Asn Asn Ser
        275                 280                 285

att atc ctc ccc cct ttt tcc ctc gcc ccc gta cct cct ccg gcg aca      912
Ile Ile Leu Pro Pro Phe Ser Leu Ala Pro Val Pro Pro Pro Ala Thr
    290                 295                 300


<210> SEQ ID NO 45
<211> LENGTH: 304
<212> TYPE: PRT
<213> ORGANISM: Human T-cell lymphotropic virus type 2

<400> SEQUENCE: 45

Met Gly Asn Val Phe Phe Leu Leu Leu Phe Ser Leu Thr His Phe Pro
1               5                   10                  15

Pro Val Gln Gln Ser Arg Cys Thr Leu Thr Val Gly Ile Ser Ser Tyr
            20                  25                  30

His Ser Ser Pro Cys Ser Pro Thr Gln Pro Val Cys Thr Trp Asn Leu
        35                  40                  45

Asp Leu Asn Ser Leu Thr Thr Asp Gln Arg Leu His Pro Pro Cys Pro
    50                  55                  60

Asn Leu Ile Thr Tyr Ser Gly Phe His Lys Thr Tyr Ser Leu Tyr Leu
65                  70                  75                  80

Phe Pro His Trp Ile Lys Lys Pro Asn Arg Gln Gly Leu Gly Tyr Tyr
                85                  90                  95

Ser Pro Ser Tyr Asn Asp Pro Cys Ser Leu Gln Cys Pro Tyr Leu Gly
            100                 105                 110

Cys Gln Ser Trp Thr Cys Pro Tyr Thr Gly Pro Val Ser Ser Pro Ser
        115                 120                 125
```

-continued

```
Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln Pro Pro Pro Thr Pro Pro Pro Leu Val His Asp Ser Asp Leu
            180                 185                 190

Glu His Val Leu Thr Pro Ser Thr Ser Trp Thr Thr Lys Met Leu Lys
        195                 200                 205

Phe Ile Gln Leu Thr Leu Gln Ser Thr Asn Tyr Ser Cys Met Val Cys
    210                 215                 220

Val Asp Arg Ser Ser Leu Ser Ser Trp His Val Leu Tyr Thr Pro Asn
225                 230                 235                 240

Ile Ser Ile Pro Gln Gln Thr Ser Ser Arg Thr Ile Leu Phe Pro Ser
                245                 250                 255

Leu Ala Leu Pro Ala Pro Pro Phe Gln Pro Phe Pro Trp Thr His Cys
            260                 265                 270

Tyr Gln Pro Arg Leu Gln Ala Ile Thr Thr Asp Asp Cys Asn Asn Ser
        275                 280                 285

Ile Ile Leu Pro Pro Phe Ser Leu Ala Pro Val Pro Pro Pro Ala Thr
    290                 295                 300


<210> SEQ ID NO 46
<211> LENGTH: 930
<212> TYPE: DNA
<213> ORGANISM: Simian T-cell lymphotropic virus type 3
<220> FEATURE:
<221> NAME/KEY: CDS
<222> LOCATION: (1)..(930)
<223> OTHER INFORMATION:

<400> SEQUENCE: 46

atg ggt aag ttt ggc ctt tat tgt ctt gtt cac ctt tac ata ctt ctc       48
Met Gly Lys Phe Gly Leu Tyr Cys Leu Val His Leu Tyr Ile Leu Leu
1               5                   10                  15

cct gcc tcc tct ggc aat ccc agt cgg tgc acc ctg ttc ata ggg gcc       96
Pro Ala Ser Ser Gly Asn Pro Ser Arg Cys Thr Leu Phe Ile Gly Ala
            20                  25                  30

tct tcc tac cac tcc agc cct tgc ggg tcc agc ctc cca cgg tgt acc      144
Ser Ser Tyr His Ser Ser Pro Cys Gly Ser Ser Leu Pro Arg Cys Thr
        35                  40                  45

tgg aat ctt gac cta ttc tcc ctc acg aaa gat caa agc cta agc ccc      192
Trp Asn Leu Asp Leu Phe Ser Leu Thr Lys Asp Gln Ser Leu Ser Pro
    50                  55                  60

cca tgt cca gac tta att act tac tca caa tac cac aag ccc tac tcc      240
Pro Cys Pro Asp Leu Ile Thr Tyr Ser Gln Tyr His Lys Pro Tyr Ser
65                  70                  75                  80

ctg tat gta ttc cct cat tgg ata act aaa cct aac cgc cgg ggc tta      288
Leu Tyr Val Phe Pro His Trp Ile Thr Lys Pro Asn Arg Arg Gly Leu
                85                  90                  95

ggt tac tat tcc gct tcc tac tca gac ccc tgt gcc ata cag tgc cct      336
Gly Tyr Tyr Ser Ala Ser Tyr Ser Asp Pro Cys Ala Ile Gln Cys Pro
            100                 105                 110

tac ctg gga tgc cag tcg tgg aca tgc ccc tat acg ggc ccg gtg tcc      384
Tyr Leu Gly Cys Gln Ser Trp Thr Cys Pro Tyr Thr Gly Pro Val Ser
        115                 120                 125

agt ccg cat tgg aga tac acc tat gat ctt aac ttt acc cag gag gta      432
```

-continued

```
Ser Pro His Trp Arg Tyr Thr Tyr Asp Leu Asn Phe Thr Gln Glu Val
    130                 135                 140

tca tcc gtc tcc tta cac ttg cat ttc tcc aaa tgc gga tcc tcg ttc      480
Ser Ser Val Ser Leu His Leu His Phe Ser Lys Cys Gly Ser Ser Phe
145                 150                 155                 160

tcc ttt cta cta gac gca cca gga tat gac cca gtg tgg ttc ctc tcc      528
Ser Phe Leu Leu Asp Ala Pro Gly Tyr Asp Pro Val Trp Phe Leu Ser
                165                 170                 175

tcc cag gcc aca cag gct cca ccc aca cct gcc cct ctc ata cgg gac      576
Ser Gln Ala Thr Gln Ala Pro Pro Thr Pro Ala Pro Leu Ile Arg Asp
            180                 185                 190

tca gat ctc cag tac att cta gaa ccg ccc att ccg tgg agc tct aag      624
Ser Asp Leu Gln Tyr Ile Leu Glu Pro Pro Ile Pro Trp Ser Ser Lys
        195                 200                 205

att ctt aac ctt atc ctc ctc acc cta aaa agc act aac tat tct tgc      672
Ile Leu Asn Leu Ile Leu Leu Thr Leu Lys Ser Thr Asn Tyr Ser Cys
    210                 215                 220

atg gtc tgt gtt gac cgc tcc agc cta tcc tca tgg cat gtc ctg tat      720
Met Val Cys Val Asp Arg Ser Ser Leu Ser Ser Trp His Val Leu Tyr
225                 230                 235                 240

gga ccc act caa gtc ccc agt cca ccc gac ccc caa gcc cgg tct atc      768
Gly Pro Thr Gln Val Pro Ser Pro Pro Asp Pro Gln Ala Arg Ser Ile
                245                 250                 255

ctg cga cct gcc tta gct att ccc gcc agt aat atc acc ccc ccg ttt      816
Leu Arg Pro Ala Leu Ala Ile Pro Ala Ser Asn Ile Thr Pro Pro Phe
            260                 265                 270

cct tgg acc cat tgc tat cgc cct cct ccg caa gcc atc tcc tcg gag      864
Pro Trp Thr His Cys Tyr Arg Pro Pro Pro Gln Ala Ile Ser Ser Glu
        275                 280                 285

aat tgt aac aac tct gta gtg ctg ccc ccc ttt tct ctg tct cca att      912
Asn Cys Asn Asn Ser Val Val Leu Pro Pro Phe Ser Leu Ser Pro Ile
    290                 295                 300

cct aac gtc tcc aga ccc                                              930
Pro Asn Val Ser Arg Pro
305                 310


<210> SEQ ID NO 47
<211> LENGTH: 310
<212> TYPE: PRT
<213> ORGANISM: Simian T-cell lymphotropic virus type 3

<400> SEQUENCE: 47

Met Gly Lys Phe Gly Leu Tyr Cys Leu Val His Leu Tyr Ile Leu Leu
1               5                   10                  15

Pro Ala Ser Ser Gly Asn Pro Ser Arg Cys Thr Leu Phe Ile Gly Ala
            20                  25                  30

Ser Ser Tyr His Ser Ser Pro Cys Gly Ser Ser Leu Pro Arg Cys Thr
        35                  40                  45

Trp Asn Leu Asp Leu Phe Ser Leu Thr Lys Asp Gln Ser Leu Ser Pro
    50                  55                  60

Pro Cys Pro Asp Leu Ile Thr Tyr Ser Gln Tyr His Lys Pro Tyr Ser
65                  70                  75                  80

Leu Tyr Val Phe Pro His Trp Ile Thr Lys Pro Asn Arg Arg Gly Leu
                85                  90                  95

Gly Tyr Tyr Ser Ala Ser Tyr Ser Asp Pro Cys Ala Ile Gln Cys Pro
            100                 105                 110

Tyr Leu Gly Cys Gln Ser Trp Thr Cys Pro Tyr Thr Gly Pro Val Ser
        115                 120                 125
```

-continued

| | | | | | | | | | | | | | | | |
|---|---|---|---|---|---|---|---|---|---|---|---|---|---|---|---|
| Ser | Pro | His | Trp | Arg | Tyr | Thr | Tyr | Asp | Leu | Asn | Phe | Thr | Gln | Glu | Val |
| | 130 | | | | | 135 | | | | | 140 | | | | |
| Ser | Ser | Val | Ser | Leu | His | Leu | His | Phe | Ser | Lys | Cys | Gly | Ser | Ser | Phe |
| 145 | | | | | 150 | | | | | 155 | | | | | 160 |
| Ser | Phe | Leu | Leu | Asp | Ala | Pro | Gly | Tyr | Asp | Pro | Val | Trp | Phe | Leu | Ser |
| | | | | 165 | | | | | 170 | | | | | 175 | |
| Ser | Gln | Ala | Thr | Gln | Ala | Pro | Pro | Thr | Pro | Ala | Pro | Leu | Ile | Arg | Asp |
| | | | 180 | | | | | 185 | | | | | 190 | | |
| Ser | Asp | Leu | Gln | Tyr | Ile | Leu | Glu | Pro | Pro | Ile | Pro | Trp | Ser | Ser | Lys |
| | | 195 | | | | | 200 | | | | | 205 | | | |
| Ile | Leu | Asn | Leu | Ile | Leu | Leu | Thr | Leu | Lys | Ser | Thr | Asn | Tyr | Ser | Cys |
| | 210 | | | | | 215 | | | | | 220 | | | | |
| Met | Val | Cys | Val | Asp | Arg | Ser | Ser | Leu | Ser | Ser | Trp | His | Val | Leu | Tyr |
| 225 | | | | | 230 | | | | | 235 | | | | | 240 |
| Gly | Pro | Thr | Gln | Val | Pro | Ser | Pro | Pro | Asp | Pro | Gln | Ala | Arg | Ser | Ile |
| | | | | 245 | | | | | 250 | | | | | 255 | |
| Leu | Arg | Pro | Ala | Leu | Ala | Ile | Pro | Ala | Ser | Asn | Ile | Thr | Pro | Pro | Phe |
| | | | 260 | | | | | 265 | | | | | 270 | | |
| Pro | Trp | Thr | His | Cys | Tyr | Arg | Pro | Pro | Pro | Gln | Ala | Ile | Ser | Ser | Glu |
| | | 275 | | | | | 280 | | | | | 285 | | | |
| Asn | Cys | Asn | Asn | Ser | Val | Val | Leu | Pro | Pro | Phe | Ser | Leu | Ser | Pro | Ile |
| | 290 | | | | | 295 | | | | | 300 | | | | |
| Pro | Asn | Val | Ser | Arg | Pro | | | | | | | | | | |
| 305 | | | | | 310 | | | | | | | | | | |